(12) United States Patent
Boctor et al.

(10) Patent No.: US 9,723,995 B2
(45) Date of Patent: Aug. 8, 2017

(54) SYSTEMS AND METHODS FOR REAL-TIME TRACKING OF PHOTOACOUSTIC SENSING

(71) Applicants: Emad Boctor, Baltimore, MD (US); Behnoosh Tavakoli, Baltimore, MD (US); Hyun-Jae Kang, Baltimore, MD (US); Xiaoyu Guo, Baltimore, MD (US); Jin Kang, Baltimore, MD (US)

(72) Inventors: Emad Boctor, Baltimore, MD (US); Behnoosh Tavakoli, Baltimore, MD (US); Hyun-Jae Kang, Baltimore, MD (US); Xiaoyu Guo, Baltimore, MD (US); Jin Kang, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 166 days.

(21) Appl. No.: 14/561,087

(22) Filed: Dec. 4, 2014

(65) Prior Publication Data
US 2015/0150464 A1 Jun. 4, 2015

Related U.S. Application Data

(60) Provisional application No. 61/911,586, filed on Dec. 4, 2013.

(51) Int. Cl.
*A61B 8/12* (2006.01)
*A61B 5/00* (2006.01)
(Continued)

(52) U.S. Cl.
CPC .......... *A61B 5/0095* (2013.01); *A61B 5/0084* (2013.01); *A61B 5/4509* (2013.01);
(Continued)

(58) Field of Classification Search
CPC .... A61B 2034/2051; A61B 2034/2055; A61B 2576/02; A61B 34/20; A61B 5/0084;
(Continued)

(56) References Cited

U.S. PATENT DOCUMENTS

2004/0064023 A1 4/2004 Ryan et al.
2005/0203399 A1 9/2005 Vaezy et al.
(Continued)

FOREIGN PATENT DOCUMENTS

WO 2013134782 A1 9/2013

OTHER PUBLICATIONS

Yuan, et al., Finite-ELement-Based Photoacoustic Tomography: Phantom and Chicken Bone Experiments, Applied Optics, 2006, 45(13): 3177-3183.
(Continued)

*Primary Examiner* — Mark Remaly
(74) *Attorney, Agent, or Firm* — Johns Hopkins Technology Ventures

(57) ABSTRACT

Systems and methods for real-time tracking of photoacoustic sensing are provided. In one aspect, a method for performing in vivo analysis of a subject is provided. The method includes directing an electromagnetic excitation toward a subject to be analyzed, and acquiring, with an ultrasound probe, data about resultant waves caused by the electromagnetic excitation. The method also includes processing the acquired data to extract information related to properties of tissues in the subject, and comparing the information related to the properties of tissues in the subject using a set of criteria. The method also includes generating a report about a condition of the subject based on the comparison of the information related to properties of the tissues in the subject.

15 Claims, 26 Drawing Sheets

(51) Int. Cl.
*A61B 8/08* (2006.01)
*A61B 5/01* (2006.01)
*A61B 34/20* (2016.01)

(52) U.S. Cl.
CPC .......... *A61B 5/7246* (2013.01); *A61B 5/7275* (2013.01); *A61B 5/7282* (2013.01); *A61B 8/485* (2013.01); *A61B 8/5253* (2013.01); *A61B 34/20* (2016.02); *A61B 5/015* (2013.01); *A61B 8/12* (2013.01); *A61B 2034/2051* (2016.02); *A61B 2034/2055* (2016.02); *A61B 2576/02* (2013.01)

(58) Field of Classification Search
CPC ..... A61B 5/0095; A61B 5/015; A61B 5/4509; A61B 5/7246; A61B 5/7275; A61B 5/7282; A61B 8/12; A61B 8/485; A61B 8/5253
See application file for complete search history.

(56) References Cited

U.S. PATENT DOCUMENTS

| | | |
|---|---|---|
| 2008/0071172 A1 | 3/2008 | Bruck et al. |
| 2008/0173093 A1 | 7/2008 | Wang et al. |
| 2009/0054763 A1 | 2/2009 | Wang et al. |
| 2009/0227997 A1 | 9/2009 | Wang et al. |
| 2010/0331707 A1* | 12/2010 | Fukutani .............. A61B 5/0073 600/476 |
| 2012/0116219 A1 | 5/2012 | Miller et al. |
| 2013/0096422 A1 | 4/2013 | Boctor et al. |
| 2013/0197344 A1 | 8/2013 | Yu et al. |
| 2013/0338504 A1 | 12/2013 | Demos et al. |

OTHER PUBLICATIONS

Wang, et al., Imaging of Joints with Laser-Based Photoacoustic Tomography: An Animal Study, Medical Physics, 2006, 33(8): 2691-2697.

Sun, et al., Three-Dimensional Photoacoustic Tomography of Finger Joint: From Phantom Experiment to In-Vivo Study, Proc. of SPIE, 2009, 7258:72584G-1-72584G-5.

Sun, et al., First Assessment of Three-Dimensional Quantitative Photoacoustic Tomography for In Vivo Detection of Osteoarthritis in the Finger Joints, Medical Physics, 2011, 38(7):4009-4017.

Izumi, et al., Ultrasonic and Photoacoustic Imaging of Knee Joints in Normal and Osteoarthritis Rats, Engineering in Medicine and Biology Society (EMBC), 2013, 35th Annual International Conference of the IEEE, pp. 1116-1119.

PCT International Search Report and Written Opinion, PCT/US2014/068650, Mar. 25, 2015, 13 pages.

* cited by examiner

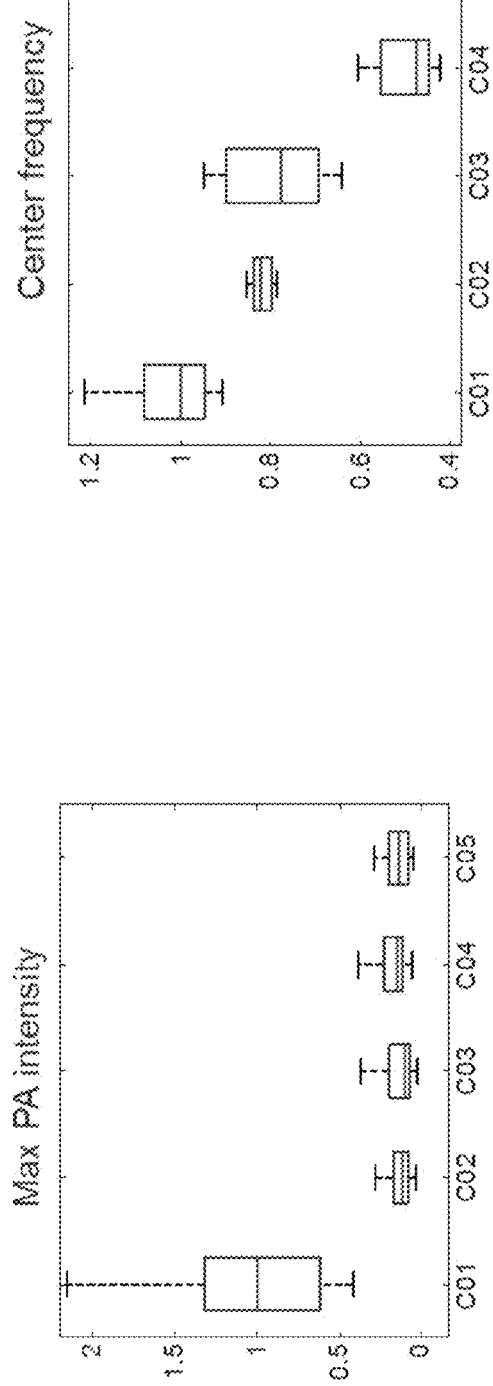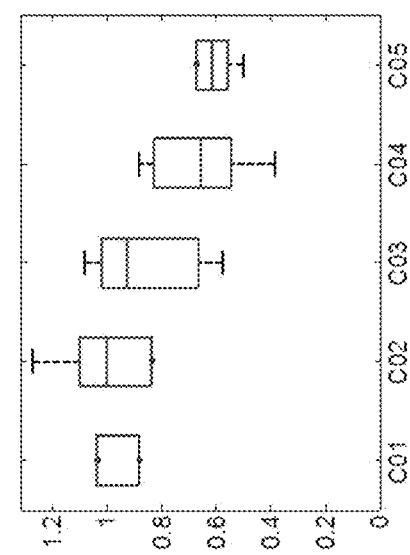
FIG. 5A
FIG. 5B
FIG. 5C

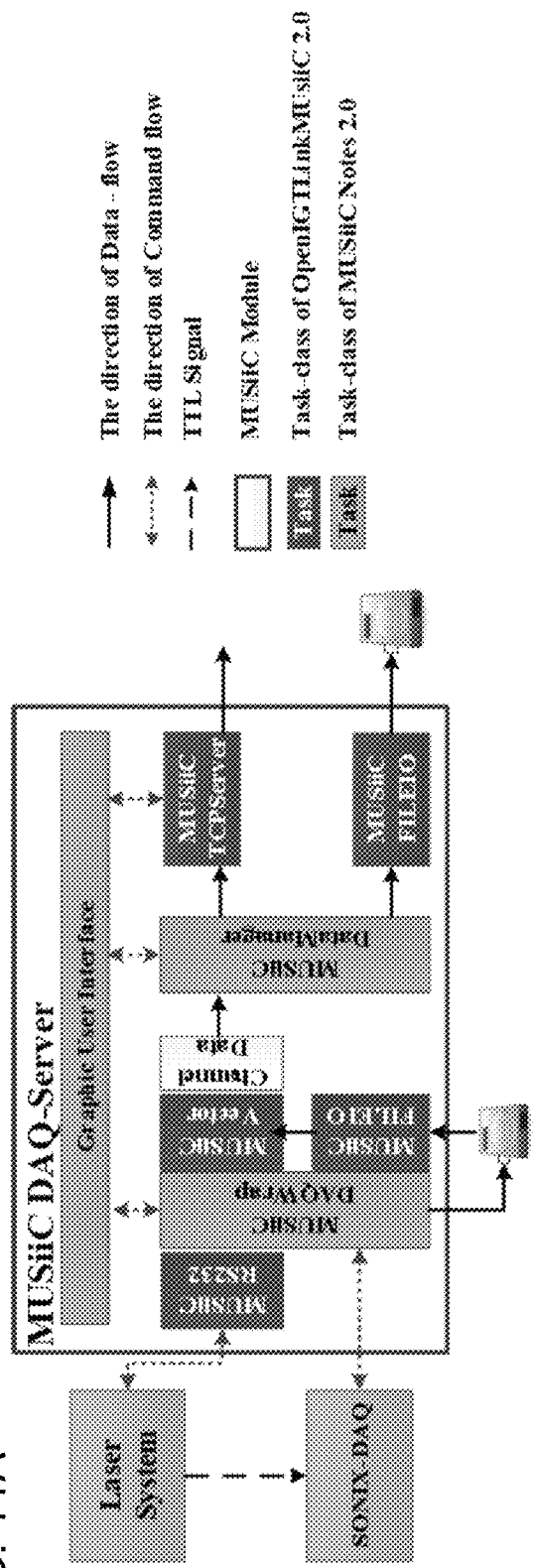
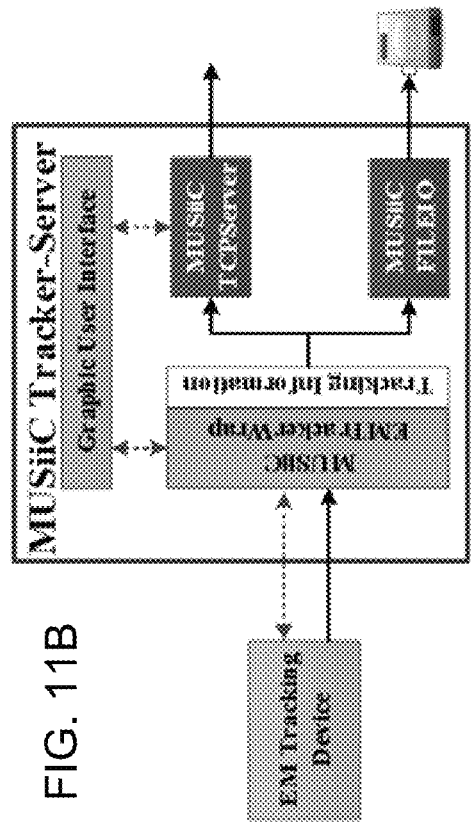
FIG. 11A
FIG. 11B

SYSTEMS AND METHODS FOR REAL-TIME TRACKING OF PHOTOACOUSTIC SENSING

CROSS-REFERENCE TO RELATED APPLICATIONS

This application is based on, claims priority to, and incorporates herein by reference in its entirety U.S. Provisional Ser. No. 61/911,586, filed Dec. 4, 2013, and entitled "SYSTEM AND METHOD FOR REAL-TIME TRACKING OF PHOTOACOUSTIC SENSING."

BACKGROUND OF THE INVENTION

The present invention relates to systems and methods for acquiring data and conducting analysis using photoacoustic spectroscopic sensing.

There are a variety of invasive and non-invasive imaging modalities in clinical use. Some have received general and substantially wide adoption for a variety of clinical applications, such as computed tomography (CT) imaging, ultrasound imaging, magnetic resonance (MR) imaging, and positron emission tomography (PET) imaging. These and other imaging modalities have been highly-specialized for particular clinical applications.

Ultrasound imaging is used in a variety of ways, including some that may be tailored to specific clinical applications. Traditional ultrasonic scanning and imaging techniques rely on an ultrasound signal that is delivered into an area of interest to interrogate the area. There are a number of modes in which traditional ultrasound system operate to produce interrogate objects. An ultrasound transmitter may be placed on one side of the object and the ultrasound signal transmitted through the object to an ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode). In either case, ultrasound signals are transmitted into the object being investigated and an ultrasound signal (transmitted signal or echo) is received to acquire the data.

In addition to these traditional imaging modalities, there are new and emerging imaging modalities. Some are hybrids of existing modalities, such as combined CT-PET or MR-PET systems. Others are new modalities or employ different or modified contrast mechanism and, thereby, provide unique clinical information.

Unfortunately, regardless of the diversity of the imaging modalities available or the combinations of known imaging modalities, each modality or hybrid of modalities has inherent limitations. Some limitations may include health limitations, such as with imaging modalities that utilize ionizing radiation. Other limitations may be inherent in the contrast mechanism employed by the modality.

Thus, there is a need for systems and methods capable of providing diverse and accurate clinical information about in vivo structures noninvasively in an efficient and effective manner.

SUMMARY OF THE INVENTION

The present disclosure overcomes the drawbacks of previous technologies by providing systems and methods capable of a wide range of application with respect to in vivo analysis of a subject. Specifically, the approach described herein relies on the photoacoustic (PA) effect, or more generally the thermoacoustic effect, by which electromagnetic energy directed to target tissues or materials is absorbed and converted to broadband acoustic signals, detectable, for example, using ultrasound techniques. Using excitation, detection and data analysis systems and methods afforded by the present disclosure, various properties of targeted tissues or structures in a subject can be obtained in vivo, such as mechanical properties, optical properties, thermal properties, and so forth, or tissues or structures, as will be described.

In accordance with one aspect of the disclosure, a system is provided for performing in vivo analysis of a subject. The system includes an excitation source configured to direct an electromagnetic excitation toward the subject, an ultrasound probe configured to acquire data about resultant waves caused by the electromagnetic excitation, and a processor. The processor is configured receive the data from the ultrasound probe, and process the received data to extract information related to properties of tissues in the subject. The processor is also configured to compare the information related to the properties of tissues in the subject using a set of criteria, and generate a report about a condition of the subject based on the comparison of the information related to properties of the tissues in the subject.

In accordance with another aspect of the disclosure, a system is provided for performing in vivo analysis of a subject. The system includes an excitation source configured to generate an electromagnetic excitation and a delivery system configured to receive the electromagnetic excitation from the excitation source and direct the electromagnetic excitation toward the subject. The system also includes an ultrasound probe configured to acquire data from the subject about resultant waves caused by the electromagnetic excitation and a holder configured to engage the ultrasound probe and at least a portion of the delivery system to provide an adjustable relative coupling between the ultrasound probe and the portion of the delivery system.

In accordance with yet another aspect of the disclosure, a system is provided for performing in vivo analysis of a subject. The system includes an excitation source configured to generate an electromagnetic excitation and a delivery system configured to receive the electromagnetic excitation from the excitation source and direct the electromagnetic excitation toward the subject. The system also includes an ultrasound probe configured to acquire data from the subject about resultant waves caused by the electromagnetic excitation and a tracking system configured to track a position of at least one of the delivery system and the ultrasound probe.

In accordance with still another aspect of the invention, a method is provided for performing in vivo analysis of a subject. The method includes directing an electromagnetic excitation toward a subject to be analyzed, and acquiring, with an ultrasound probe, data about resultant waves caused by the electromagnetic excitation. The method also includes processing the acquired data to extract information related to properties of tissues in the subject, and comparing the information related to the properties of tissues in the subject using a set of criteria. The method further includes generating a report about a condition of the subject based on the comparison of the information related to properties of the tissues in the subject.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 5A through 5C are graphs showing the maximum intensity, center frequency, and the bandwidth of detected PA signals at different wavelengths using the systems of FIG. 1.

FIGS. 11A and 11B are block diagram depicting modules in the software framework of FIG. 10.

DETAILED DESCRIPTION OF THE INVENTION

The present disclosure is directed to systems for tracked photoacoustic (PA) scanning, including spectroscopic scanning and/or compounding imaging. The present disclosure also provides methods for scanning, sensing, processing, and generating images and spectroscopy data specifically using PA systems, and thermoacoustic systems, in general. PA scanning is an emerging technology developed for a number of biomedical purposes. It uses the PA effect, by which electromagnetic energy is absorbed by a target material and converted to a detectable broadband acoustic signal. This occurs due to rapid thermoelastic expansion and contraction. The produced expansion and contraction then induces a resultant wave that propagates in all directions and can be detected by, for example, ultrasound transducers or hydrophones. Clinically, PA sensing is advantageous as a real-time functional modality given its potentially low cost, portability, and ease of operation.

In particular, the initial pressure generated in a targeted tissue or structure is proportional to light fluence of the excitation beam when the pulse in the excitation beam is smaller than thermal and stress relaxation time. That is initially pressure may be described by P∝Γ×Optical Absorption×Light Fluence, where:

$$\Gamma = \frac{B\beta}{\rho v_s} \quad (1)$$

where B is bulk modulus, β is the volume thermal expention, ρ is density and $v_s$ is the speed of sound. That is, photoacoustic wave generation is governed by optical and mechanical properties of the targeted tissue or structure, while the propagation of the generated wave depends on intrinsic elastic properties and mass density of the traversed medium. Therefore, in accordance with the present disclosure, wave data properly acquired and analyzed may be utilized to reveal a variety of characteristics or properties of tissues and structures in a subject.

Figure 1A:
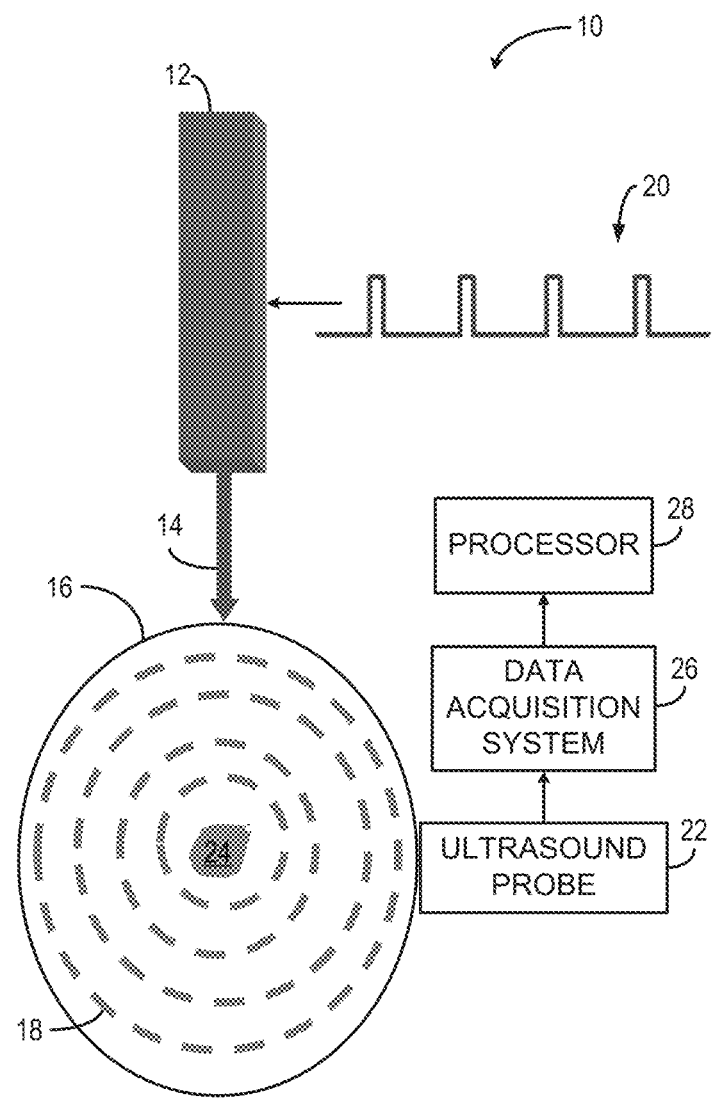
FIG. 1A is an schematic diagram of a system in accordance with the present disclosure.

Referring now to FIG. 1A, a schematic illustration of a PA scanning system 10 is illustrated, in accordance with general aspects of the present invention. Specifically, the system 10 includes a photoacoustic excitation source 12 configured to transmit disturbances 14 into a subject 16 to induce propagating waves 18 thereabout, where the photoacoustic source 12 can be arranged in proximity to or remote from the subject 16.

In some aspects, the photoacoustic excitation source 12 may be, for example, a laser source, a microwave source, or other electromagnetic source, and configured to produce acoustic signals in the subject 16 using the modulating signal 20 provided by a driving circuit (not shown in FIG. 1A). The disturbances 14 may be any electromagnetic disturbance, such as a laser beam, a microwave, or other electromagnetic wave, configured or modulated in a manner consistent with particular application of PA scanning system 10. In some aspects, the disturbances 14 may be in the form of pulsed or modulated light, or a coded excitation, and described by various or multiple amplitudes, wavelengths, phases, frequencies, ranges thereof, and so on, and any combinations thereof.

The system 10 also includes a sensor 20, for example, an ultrasound probe 22, which may be an array of receivers or a single receiver or transducer, positioned to collect data about the resultant waves 18 and, thereby, structures 24 within the subject 16. A data acquisition system 26 may be coupled to the ultrasound probe 22 to receive the acquired data. Also, a processor 28 may be coupled to the data acquisition system 26, and configured to receive the acquired data and process it in a manner consistent with desired properties of targeted tissues or structures, as well as the disturbances 14 provided. By way of example, processor 28 may be configured to analyze signal features associated with acquired acoustic data, such as signal amplitudes, spectral components, bandwidths, phases, frequency, and so forth, and/or changes thereof. In some aspects, processor 28 may be further configured to compare the analyzed signal features to a reference or a standard according to a set of criteria. For instance, such reference or standard can be stored in a memory accessible by the processor 28 and include signal features found in a population, or previously acquired baseline or dataset from the subject, or signal features associated with specific conditions or known or controllable tissue or structure properties.

Figure 1B:
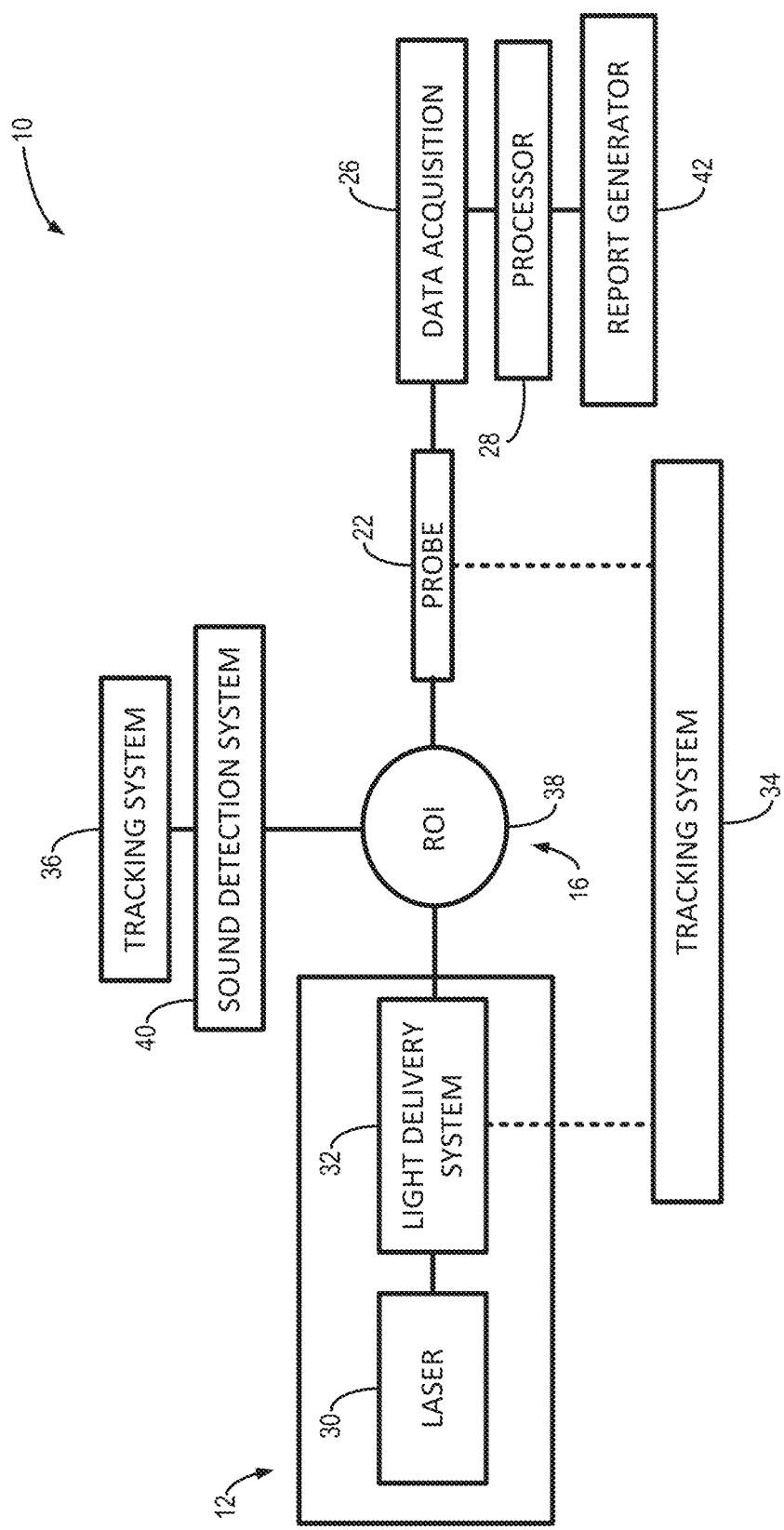
FIG. 1B is a schematic block diagram of a system in accordance with the present disclosure.

Referring to FIG. 1B, a schematic illustration of the system 10 is provided. As illustrated, system 10 operates using a photoacoustic excitation source 12, which may include a laser 30 and light delivery system 32, and an ultrasound probe 22. By way of example, light delivery system 32 can include a number of optical waveguides or optical fibers capable of directing an excitation beam of photons to a region of interest (ROI) 38.

Coupled to the light delivery system 32 and/or probe 22 may be a tracking system 34. As will be described, the tracking system 34 may take a variety of forms that may include, for example, tracking systems such as described in co-pending U.S. patent application Ser. No. 13/476,838, published as US2013/0016185, which is incorporated herein by reference in its entirety. In this regard, the system 10 may be integrated with infrared (IR) monitoring and video cameras that can be communicated to a projector. In this regard, as will be described, tracking can be performed to perform the registration and visualization. That is, a tracking system 36 may be used to track the subject 16 and, in particular, a ROI 38 in the subject 16. Also, a sound detection system 40 may be used to monitor the ROI 38.

As described, an ultrasound probe 22 is used to collect data from the ROI 38. The probe 22 is coupled to a data acquisition system 26 and processor 28. Furthermore, the processor 28 may be coupled to a report generator 42 to provide feedback to a clinician. The report generator 42 may include a display system, a printing system, or other system for generating reports that include visual or auditory information to a user or clinician. For instance, the report may be communicated to tablet devices, local webpages utilizing via Wi-Fi or Bluetooth communication protocols.

In function, the laser 30 generates an excitation beam that is guided by the light delivery system 32 to excite the subject 16 and, in particular, the ROI 38 in the subject 16. The probe 22 monitors the subject 16 and, in particular, the ROI 38 to acquire raw data that is passed to the data acquisition system 26 and processor 28 for processing. For example, the ROI 38 may be illuminated with multiple wavelengths, while the generated PA signal is detected with the probe 22 and data acquisition system 26 in real-time or near real-time. In some aspects, coded laser pulses including multiple wavelengths can be applied simultaneously. Thus, in addition to improving the SNR, the time cost associated with acquiring multispectral information sequentially may be reduced. The spectral components may then be separated from the detected signal.

A variety of sources can be used as the PA excitation source 12 to generate excitation beams. For instance, laser diodes may be advantageously utilized, having a higher pulse repetition rate in comparison to solid state lasers. Although laser diodes have comparatively lower power, which can lead to a lower signal-to-noise ratio (SNR), signal averaging along with coded excitation methods may be utilized to enhance SNR. For example, pseudorandom sequences can be used to generate multispectral coded excitations.

As described, in addition to light being used source to generate a PA effect, other electromagnetic waves (for example microwaves) can cause a similar effect, often referred to with thermoacoustic effect. Hence, the photoacoustic excitation source 12 can alternatively be a microwave source, or other electromagnetic, separate from or combined with the ultrasound probe 22.

The data acquisition system 26 and processor 28 may be configured to perform a number of pre-processing steps, including filtering and basic extraction of the raw data. In some aspects, raw signal data may be assembled using time and/or frequency representations. In addition, data acquisition system 26 and processor 28 may be configured to acquire and process data to generate one or more images of the subject. Other processing steps be performed, including signal averaging or tracker-based compounding, to increase a SNR or contrast-to-noise ratio (CNR) of the acquired raw data.

The processor 28 may be configured to process signal data and extract particular signal characteristics therein. For instance, such signal characteristics can include maximum intensity in the time domain, center frequency, and bandwidth in the frequency domain, and so on. In some aspects, the processor 28 may analyze the extracted features or characteristics associated with acquired signal data and using, for example, a machine learning method, such as Support Vector Machine, classify the ROI 38 as normal or abnormal.

In some aspects, processor 28 may also be configured to separate acquired signals into components from individual tissue absorbers using photoacoustic absorption spectra generated therefrom. In this manner, such separated signals may then be utilized by processor 28 to generate images indicative of specific tissue materials. Specifically, a decomposition algorithm for un-mixing photoacoustic absorption spectrum may be applied by processor 28. The intensity of generated PA signal can be formulated as: $PA_{total} = \Gamma \Phi \mu_{total}$, $\mu_{total} = \Sigma_{m=1}^{M} C_m \epsilon_m(\lambda)$ where $\Gamma$ is Gruneisen constant for converting absorbed optical energy into acoustic pressure, $\Phi$ is laser fluence in $J/cm^2$, $\mu_{total}$ is total absorption coefficient in $cm^{-1}$, $\lambda$ is wavelength in nm, $C_m$ is concentration of mth absorber, $\epsilon$ is extinction coefficient and M is number of absorbers in the ROI. It is also possible to rewrite the PA signal equation as weighted combination of photoacoustic signal of all absorbers as following: $PA_{total} = \Sigma_{m=1}^{M} C_m PA_{ref\_m}(\lambda)$ where $PA_{ref\_m}$ is the reference PA spectrum of mth absorber normalized to its concentration. The processor 28 may then solve a minimization problem for unknown concentration/weight of each absorber: $Min \|PA_{total} - PA_{ref} C\|^2$.

Figure 15:
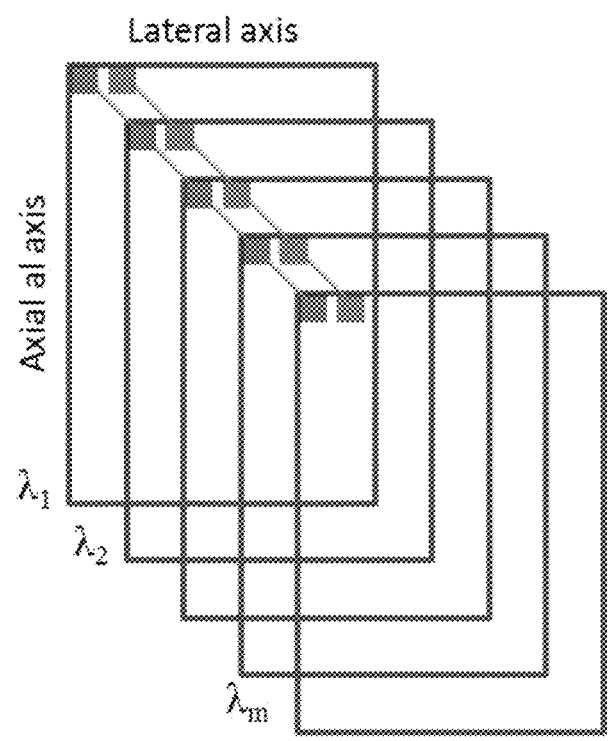
FIG. 15 is a graphical illustration depicting a data processing approach, in accordance with aspects of the present disclosure.

The spectral decomposition problem may be solved with nonnegative linear least square optimization method along with localized regularization. In this approach, photoacoustic spectrum of each pixel is extracted from images acquired at multiple wavelengths as shown in FIG. 15. With localized regularization, PA spectrums of the neighboring pixels are included in solving the minimization problem for the unknown weight of each absorber per pixel. In the matrix form $[PA_{total}]_{N*L}$, $[C]_{N*M}$ and $[PA_{ref}]_{M*L}$ where N is number of pixels in the window while the chosen pixel located at the center and L is number of imaging wavelengths. There are M unknowns and L linear equations where normally L>>M. By solving this minimization for all pixels in a ROI, the concentration map or weight distribution of each absorber may be reconstructed.

Figure 16:
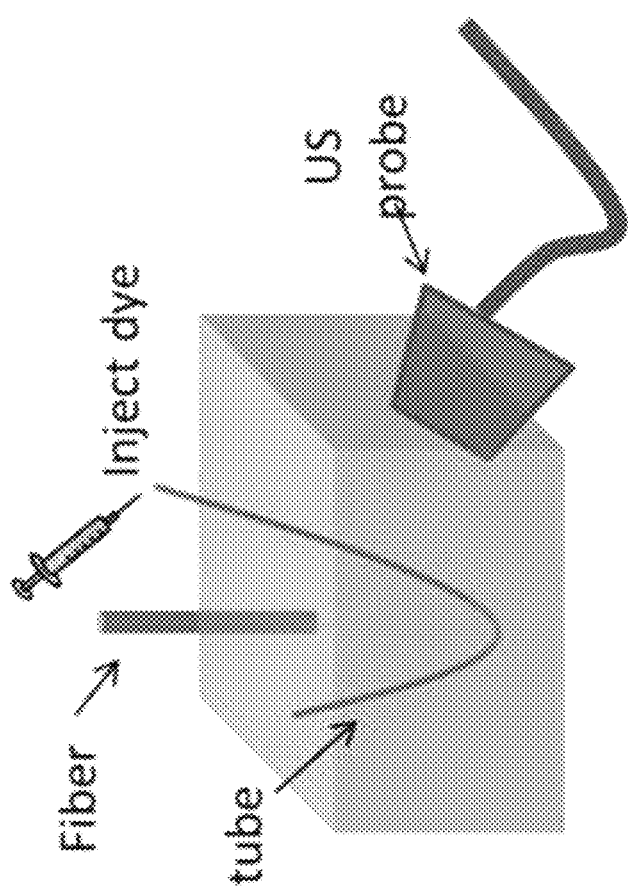
FIG. 16 is an example of an experimental setup for a phantom study, in accordance with aspects of the present disclosure
Figure 17A:
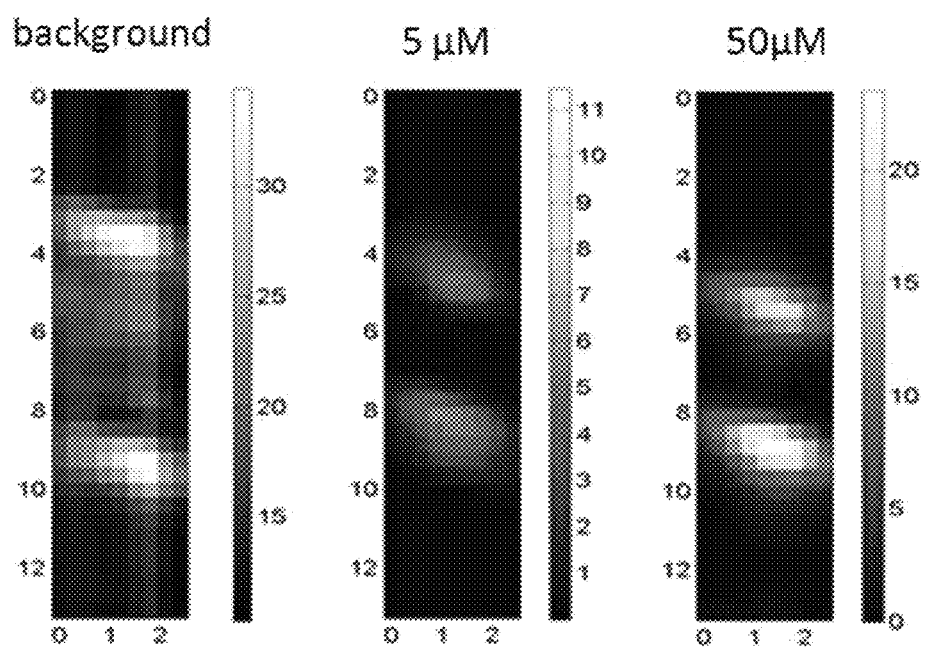
FIGS. 17A and 17B are example concentration maps generated using an approach in accordance with aspects of the present disclosure.
Figure 17B:
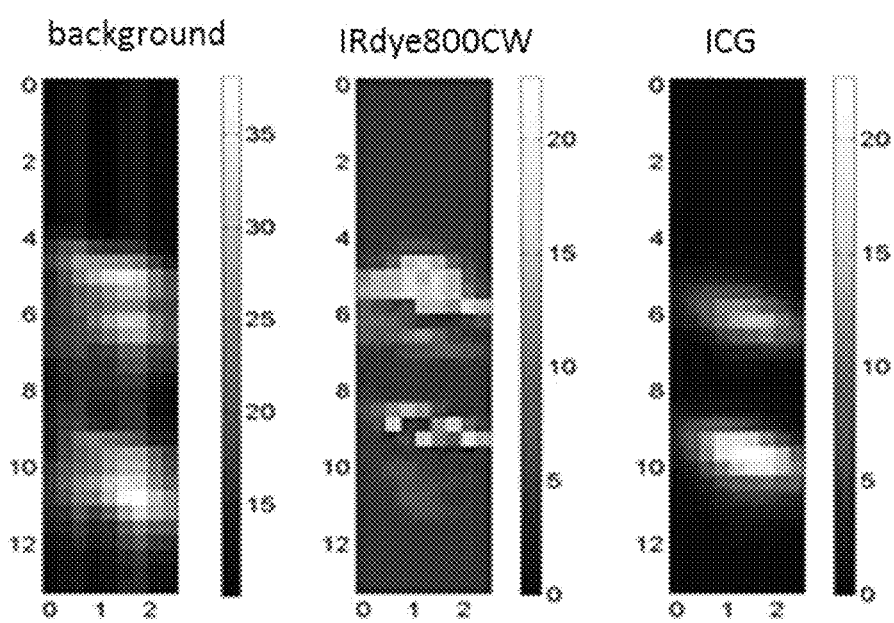

In one application, this approach may be applied to estimate concentration maps. By way of example, concentration maps of dyes were generated using the experiment setup shown in FIG. 16. Specifically, FIG. 17A shows results comparing 5 μM and 50 μM contrast agent based on ICG, and it was observed that 50 μM dye generated about 4.4 times higher PA signal in comparison to 5 μM one. In addition, images were also produced of an equal mixture of 50 μM of this dye with 50 μM of another contrast agent based on IRdye800CW and their corresponding concentration maps, are shown in FIG. 17B. The relative concentration for these dyes was calculated to be 1.16.

Figure 18:
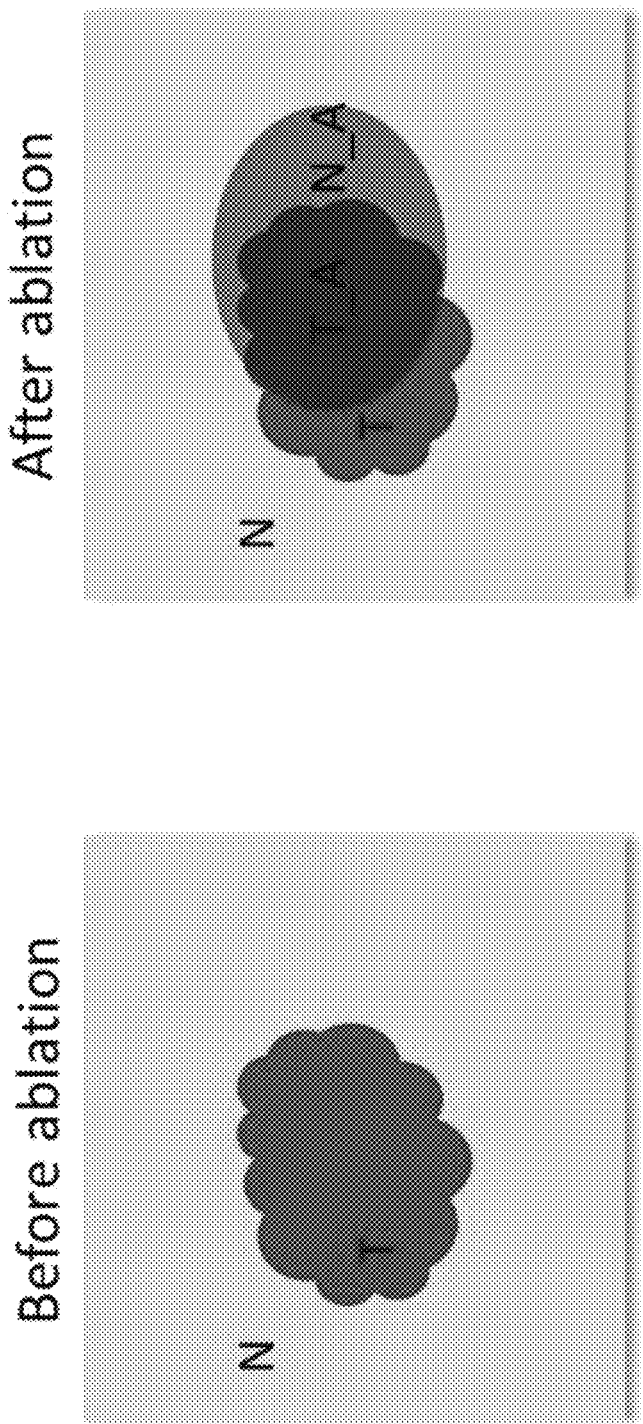
FIG. 18 is a schematic illustrating differences between tissues after ablation.

In some applications, the above-described approach of spectral decomposition can be applied for cancer imaging using targeted contrast agents. It can also be used for tissue characterization for instance in ablation monitoring application to identify remaining non-ablated tissue. In particular, after ablation, an ROI can be decomposed to four tissue types including normal (N), tumor (T), ablated normal (N_A), and ablated tumor (T_A), as shown schematically in FIG. 18. Since the optical absorption spectrum and consequently photoacoustic spectrum of these tissues are different, it is possible to solve the un-mixing photoacoustic spectroscopy problem to estimate weight of each tissue type per area and eventually estimate the region of non-ablated tumor.

The processor 28 may also communicate any information associated with raw and processed data to a user or clinician via a report generated by report generator 42. For example, the report may include information about the density and mechanical structure of the tissues or structures in the ROI 38. Also, such information may provide an indication to a clinician regarding the presence or properties of normal, ablated normal, tumor and ablated tumor tissues. In some aspects, the report generator 42 may provide a report that includes one or more generated images, or images averaged or compounded, for example, using a spatial-angular compounded technique.

The tracking system 32, 36 may be multiple or a single, coordinated system. To aid the user or clinician in operating the system 10 effectively and efficiently, the tracking systems 34, 36 may be included. The tracking systems 34, 36 may use electromagnetic (EM), optical, or other detection mechanisms to track the absolute and/or relative positioning of the excitation source 12 and subject 16, generally, and the excitation beam 14 and ROI 38, in particular. For example, the tracking systems 34, 36 may be used to facilitate image registration and/or real-time tracking to guide the delivery of excitation beams from the laser 30 to the ROI 38 and guide the sound detection apparatus 40 of FIG. 1B to the position where its field of view overlaps the illuminated ROI 38.

Figure 1D:
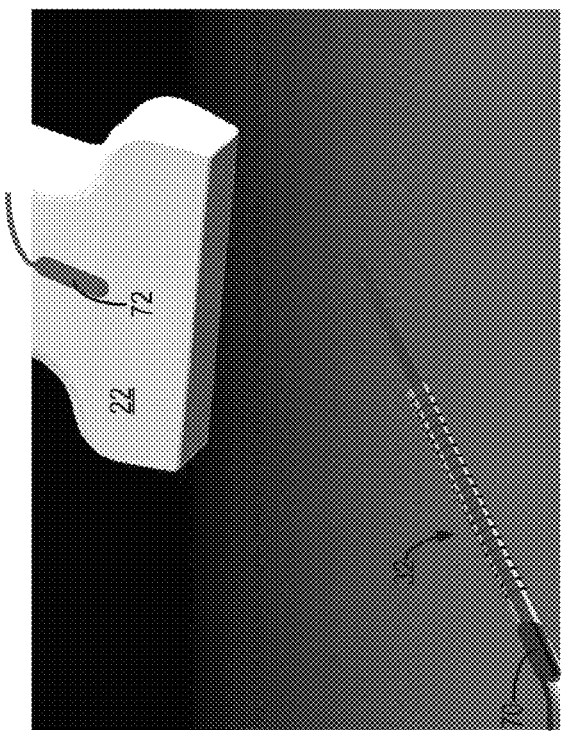
FIG. 1D is a perspective view of another example of a system of FIG. 1B.
Figure 1C:
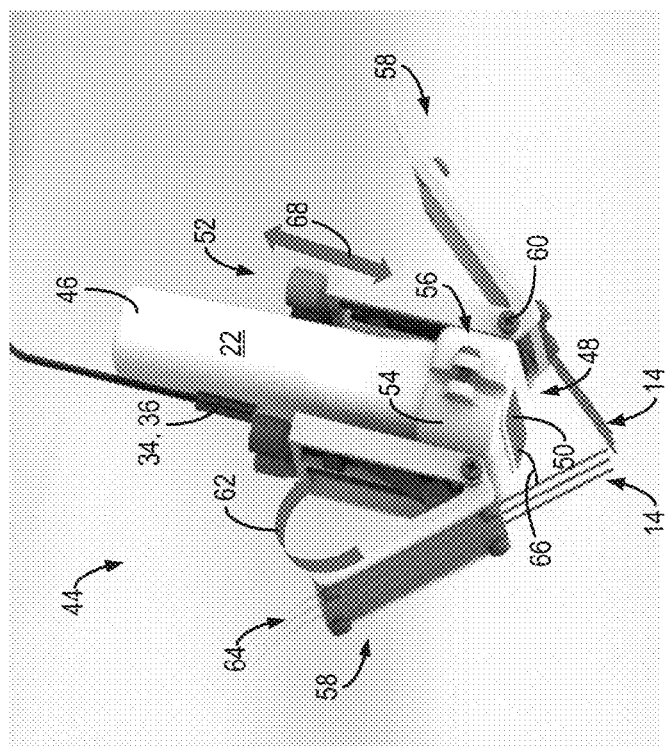
FIG. 1C is a perspective view of a holder system in accordance with the present invention coupled to one example of a system of FIG. 1B.

Referring to FIG. 1C, a combined, excitation, tracking, and probe configuration 44 is illustrated. The configuration 44 includes an ultrasound probe 22 that extends from a proximal end 46 to a distal end 48 that includes an ultrasound sensing element or elements 50. The distal end 48 is engaged by a probe holder 52. The holder 52 includes a housing 54 that may be designed to be secured to the distal end 48 using a clamping system 56.

One or more fiber holders 58 may be slidably and rotatably deployed from the housing 54. Thus, multiple degrees of freedom are provided between the holder 52, the probe 22, and the light delivery system 32. The reconfigurable fiber, attached to the ultrasound probe, can be actively actuated with more degrees of freedom. Multiple wavelengths can be fired simultaneously from different fibers and it can be dynamically formed mechanically or optically. In some aspects, the source of optoacoustic excitation can be in the form of microwave or x-ray pulses. Thus, the one or more fiber holders 58 can include microwave waveguides or other waveguides.

That is, the fiber holders 58 may rotate about a hinge 60 to rotatably adjust an angle of deployment 62. The fiber holders 58, thus, can arrange coordinate or control the light deliver systems 32 of FIG. 1B, such as fiber-optic waveguides 64, to be secured thereto to adjust an angle 66 for delivery of the excitation beam 14. Likewise, the fiber holder 58 may be slidably moved along a path 68 to further allow user adjustment.

Referring to FIG. 1D, the excitation source light delivery system 32 and the probe 22 may be separated and, thus, have separate tracking systems 70, 72, respectively. In the illustrated configuration, the probe 22 may be placed on top of the skin or very close to the ROI 38 of FIG. 1B. The light delivery system 32 may include an interventional or minimally interventional device, such as a probe, needle, or catheter 74. The probe or needle 74 may be designed to be inserted into the subject and proximate to or into the ROI. In this regard, the tracked excitation beam 14 is delivered in a minimally-invasive approach using the needle or catheter 74, which may be a sub-mm needle or catheter. This configuration may be particularly useful in, for example, clinical application such as deep bone scanning. Also, the light delivery system 32 can be integrated into a robotic tool. For example, the light delivery system 32 may be used with a snake robot, for example, to treat bone osteoylsis. The sensing fibers including light and acoustic sources and transmitters can be integrated in the snake-robot channels. The spectroscopic PA imaging can differentiate internal bone osteoylsis and identify boundary between normal tissue, osteolysis, and injected material. Furthermore, the system may be configured as a single-tracked sensor that is lightweight and includes a single ultrasound element with light delivery and tracking elements. In the case of a catheter, the catheter may be used in combination with a vascular catheter, or other catheter or device for use in a clinical process.

Figure 1E:
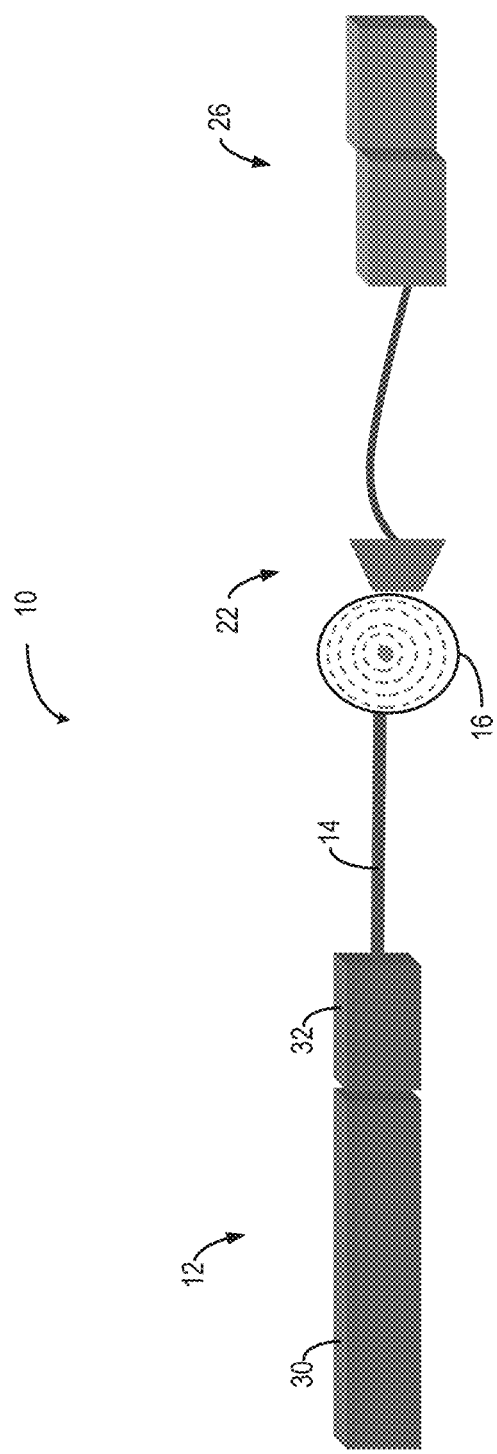
FIG. 1E is a schematic diagram of a system in accordance with the present disclosure used to acquire experimental data.

Referring to FIG. 1E, a particular configuration of the system 10 of FIGS. 1A and 1B is illustrated that includes a tunable laser 30, such as a Q-switch Nd:YAG laser, followed by a light delivery system 32 that includes an optical parametric oscillator (OPO) system generating pulses at a wavelength range of, for example, 690 nm-950 nm, such as is desirable, for example, for to differentiate normal and osteoporotic bone. The photoacoustic signal is detected with the ultrasound probe 22, which is coupled to the data acquisition system 26. The ultrasound probe 22 and data acquisition system 26 may, for example, be a Sonix RP system such as is available from Analogic.

Figure 2:
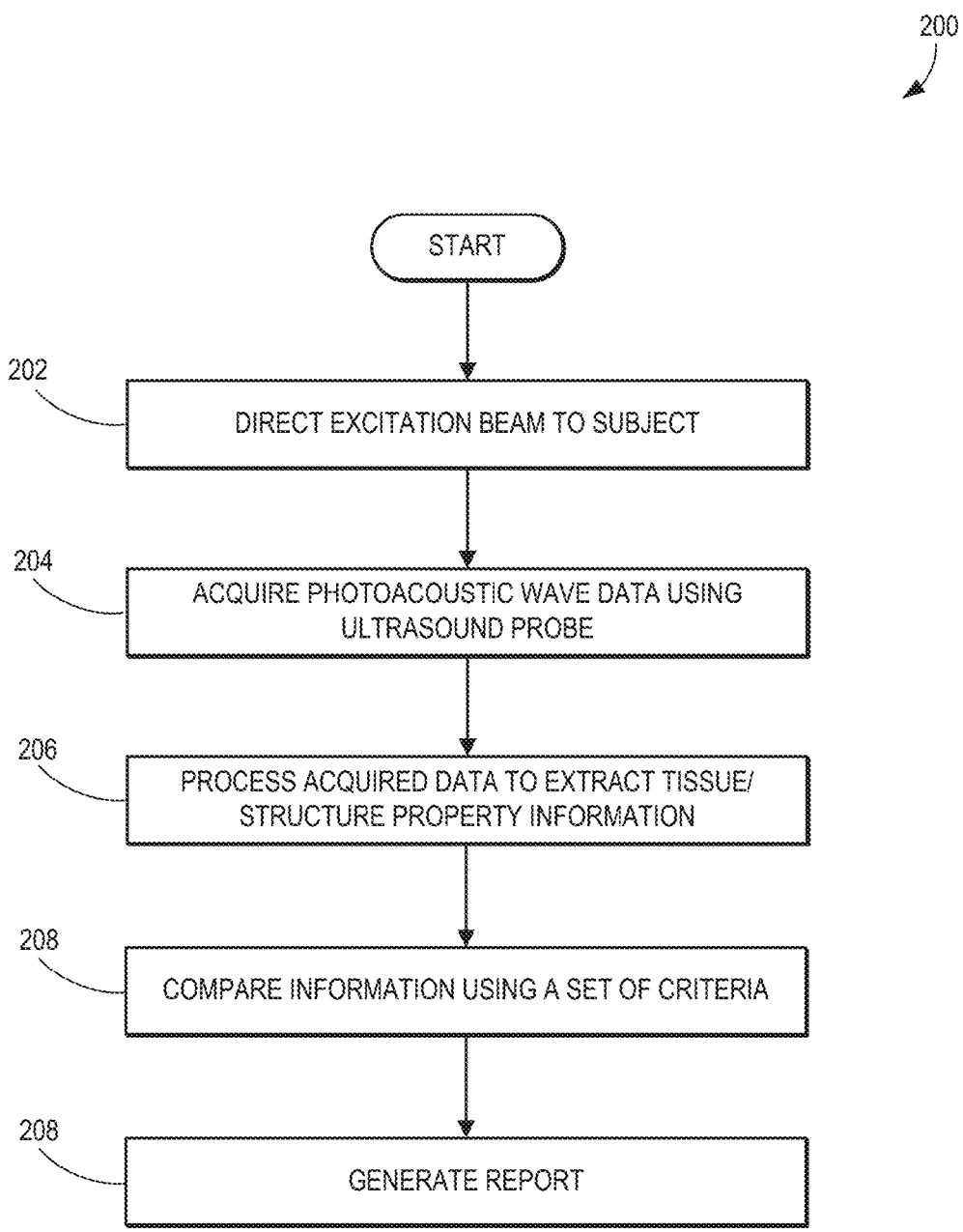
FIG. 2 shows steps of an illustrative process for performing in vivo analysis of a subject, in accordance with aspects of the present disclosure.

Turning to FIG. 2, steps of a process 200 for performing in vivo analysis of a subject, in accordance with aspects of the present disclosure, are shown. In particular, process 200 may be implemented using systems described with reference to FIGS. 1A-1E, or other PA systems. The process 200 may begin at process block 202 by directing an excitation beam of photons toward a subject to be analyzed along any number of directions, and acquiring, with an ultrasound probe, data about resultant waves caused by the excitation beam, as indicated by process block 204. As described, the excitation beam of photons may be in the form of a laser beam, and configured in a manner consistent with particular application. For example, the excitation may be in the form of pulsed or modulated light, described by various or multiple amplitudes, wavelengths, phases, frequencies, and so on, and any combinations thereof.

As indicated above, acquired data may be subjected to a number of processing steps, including filtering and basic extraction of the raw data, for instance during process block 204, as well as signal averaging or compounding after data acquisition, to increase a SNR or contrast-to-noise ratio (CNR) of the acquired raw data, at process block 206. For instance, processing steps may be performed to identify various signal features associated with the acquired and/or processed acoustic data, such as signal amplitudes, spectral components, bandwidths, phases, frequency, and so forth, and/or changes thereof. In some aspects, raw or processed data may be processed at process block 206 to extract information, related to properties of targeted tissues or structures in the subject, such as mechanical properties, or optical properties, or thermal properties, or combinations thereof. In addition, raw or processed data and any information therefrom may be used to generate one or more images of the subject.

Then, at process block 208, information related to properties of targeted tissues or structures in the subject may then be compared, using a set of criteria. In particular, such information may be compared to a standard or reference dataset, such as a population dataset, a baseline dataset or a prior dataset acquired from the subject, to determine a condition of the subject. Specifically, the comparison criteria can depend upon the nature of the excitation provided, the particular property under analysis, measurement configurations, characteristics, conditions, and so forth. In this manner, for example, a determination can be made regarding the presence of an osteoporotic bone, or an indication of a low or a high bone density of the subject.

In some aspects, a spectroscopic analysis of the data may be performed to generate spectroscopy information. In spectroscopy, by changing the wavelength of the excitation source, it is possible to analyze various spectral components to identify specific properties of the target tissues or structures. For example, mechanical properties and changes thereof, such as young's modulus, compressive strength, and so on, may be determined and tracked using spectroscopy information along with the signal analysis in the frequency domain. In this manner, for example, the presence of osteoporotic bone can be determined, as well as a susceptibility to fracture. On the other hand, the optical properties of the osteoporotic bone such as optical absorption may be evaluated using photoacoustic spectroscopy. Features in photoacoustic signal may correlate with both optical and mechanical parameters of bone.

Process blocks 202 and 206 may be repeated for any number of configurations with respect to the spatial orientation of the excitation beam and measurement direct. As such, a number of views may be obtained and combined for various tissues or structures in the subject. In this manner, one-, two-, or three-dimensional renderings or representations of the subject may constructed using the various views obtained.

At process block 208, a report, of any form, may be generated based on obtained information in relation to properties of the tissues in the subject. For instance, the report may be indicate results from the comparison to the standard or reference, and/or an indication of the likely in vivo pathology or a condition of the subject. In addition, the report may include one or more images, renderings or representations of the subject and/or tissues or structures therein, or combinations thereof.

Figure 22:
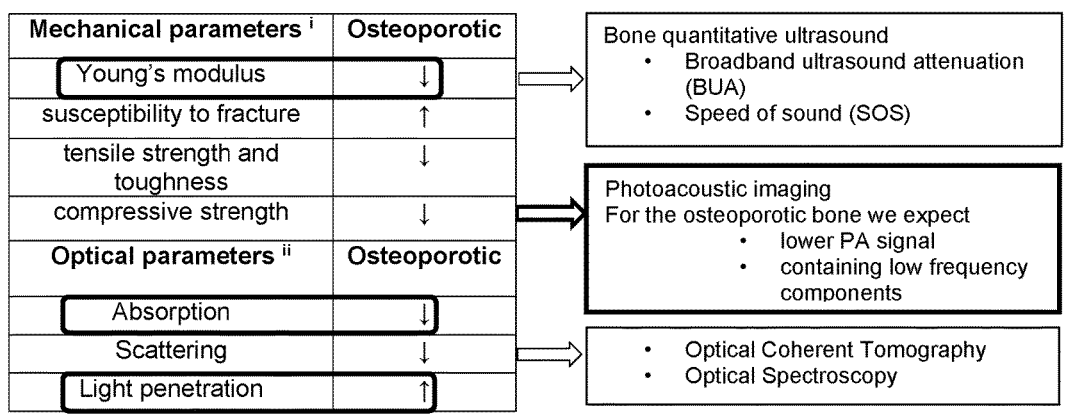
FIG. 22 illustrates correlations of features extracted using the present invention when applied to bone analysis and, in particular analysis of osteoporotic bone.

By way of example, FIG. 22 provides correlations of features extracted using the present invention when applied to bone analysis and, in particular analysis of osteoporotic bone.

Figures 3A, 3B:
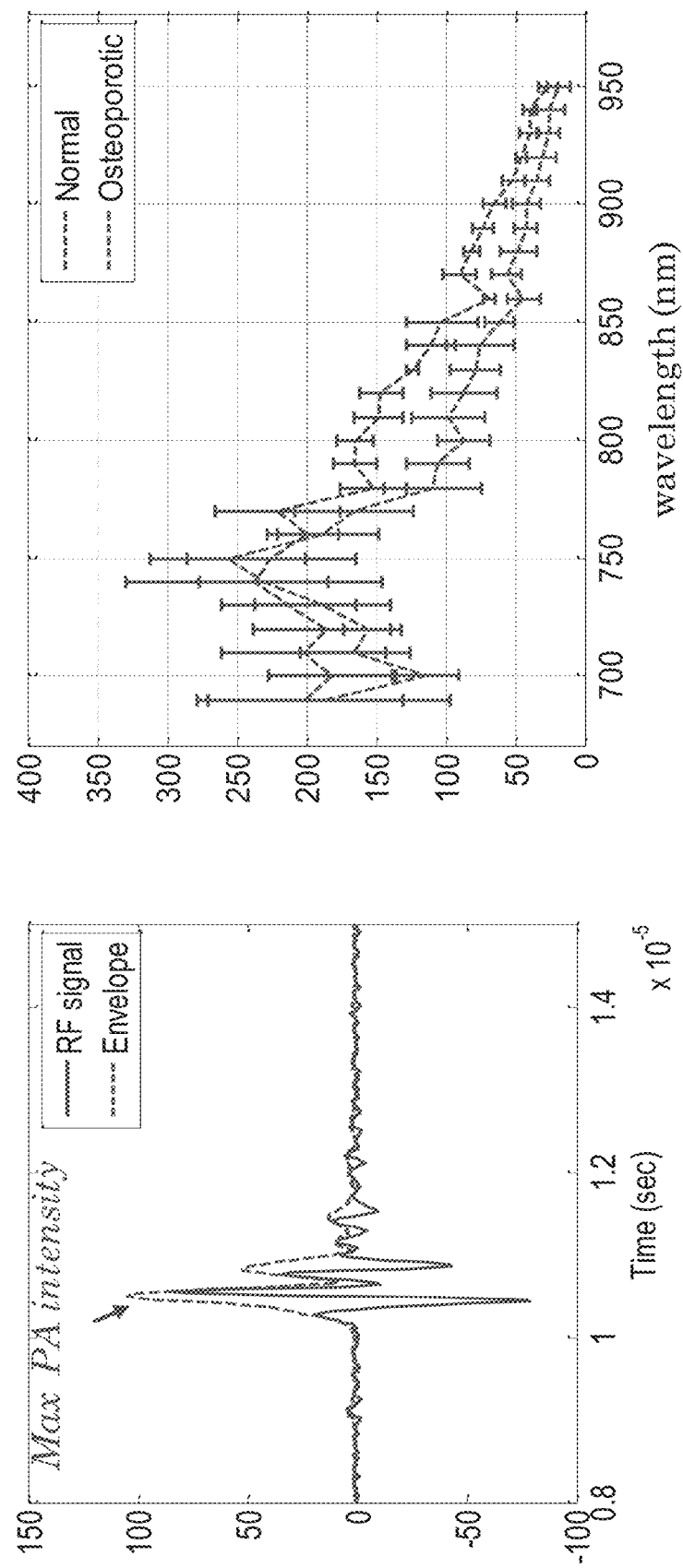
FIG. 3A is a graph showing an example of a detected signal associated with using the system of FIG. 1E to differentiate normal and osteoporotic bone.
FIG. 3B is a graph illustrating maximum PA intensity using the system of FIG. 1E to differentiate normal and osteoporotic bone.

As mentioned, one exemplary use of the above-described approach may include differentiating normal and osteoporotic bone. In accordance with one example, the subject 16, with reference to FIG. 1B, was a phantom. The speed of sound and broadband ultrasound attenuation of the imaged phantoms mimicking normal and osteoporotic bone are listed in Table 1. Multiple points of the phantom were evaluated, for example, using a linear US probe with 128 elements. Finally, the maximum raw data was extracted from the elements and plotted versus different wavelengths. The result revealed a general decrease in the spectrum of the osteoporotic phantom compared to the normal one. FIG. 3A is a graph showing an example of a detected signal used to differentiate normal and osteoporotic bone. FIG. 3B is a graph illustrating maximum PA intensity at multiple wavelengths used to differentiate normal and osteoporotic bone. Based on such analysis, Table 1 can be produced:

TABLE 2

| Quantitative ultrasound heel phantom (CIRS inc.) | | |
|---|---|---|
| | BUA (dB/MHz) | SOS (m/s) |
| C01: normal | 75 | 50 |
| C02: osteoporotic | 1560 | 1520 |

Figure 4B:
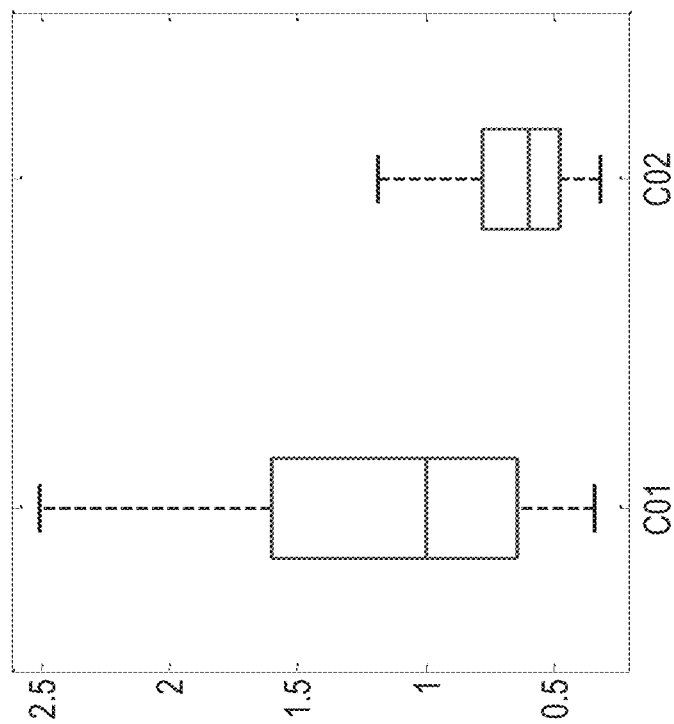
FIGS. 4A through 4E are graphs illustrating data acquired from PA signal detected with 128-element linear US probe in the reflection mode using the systems of FIG. 1.
Figure 4A:
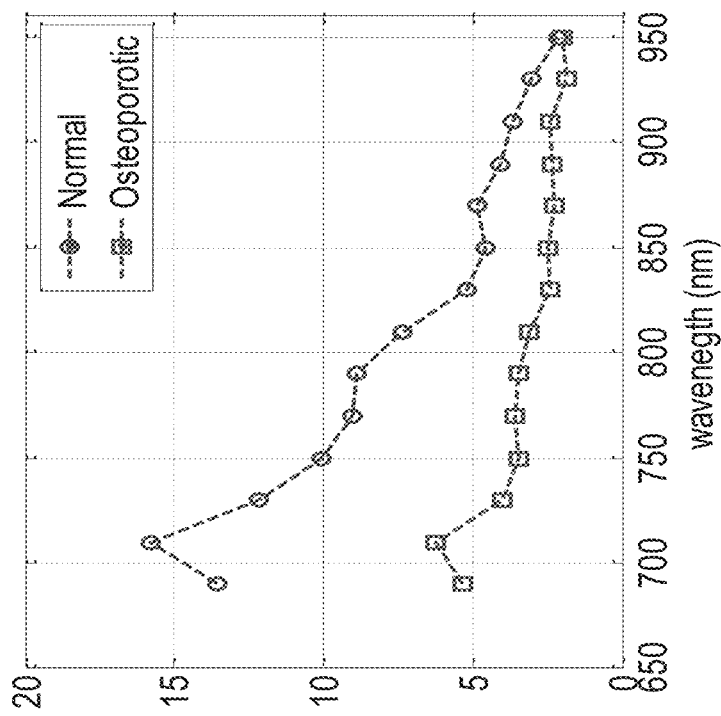
Figure 4D:
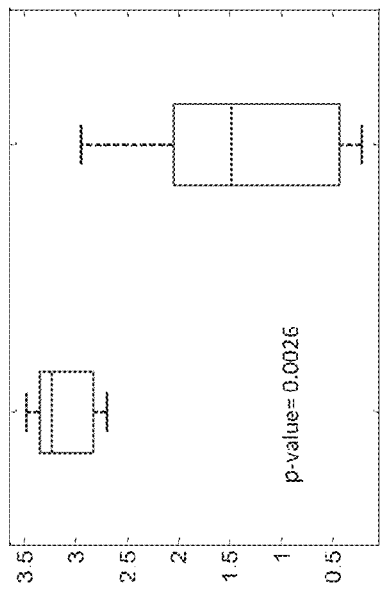
Figure 4E:
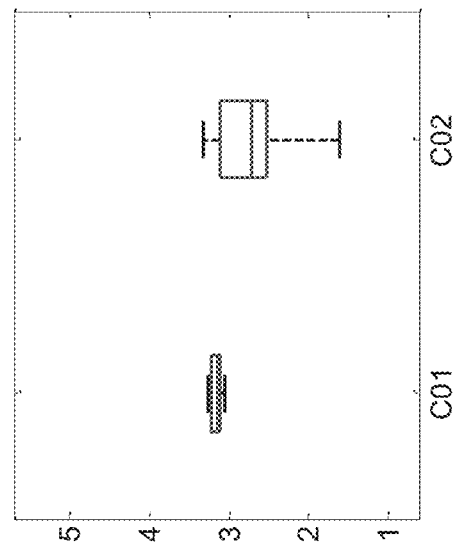
Figure 4C:
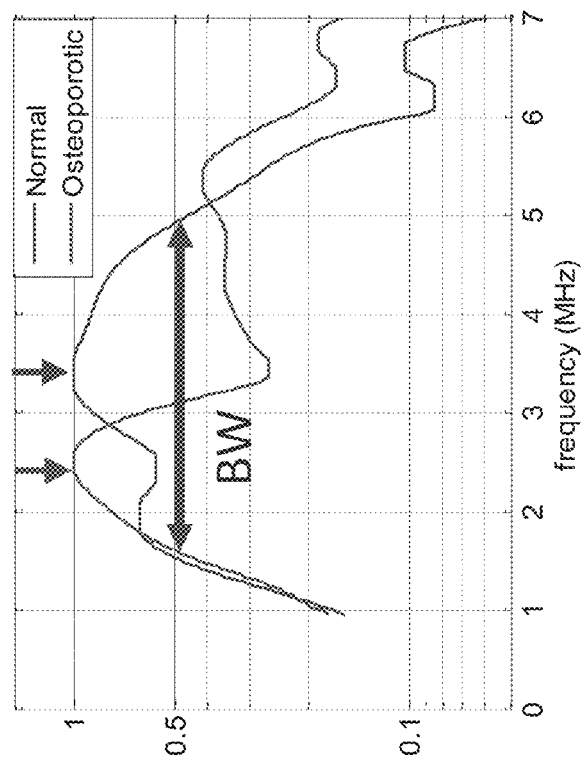

Referring now to FIGS. 4A through 4E, the above-described setup may be modified such that the laser light is coupled to the optical fiber to illuminate bone specimens and the PA signal is detected with 128-element linear US probe in the reflection mode. Using this configuration, an experiment was performed using two samples of cadaver femur neck with significant difference in the bone mineral density that was measured by dual energy x-ray absorptiometry (DEXA), as shown in Table 2. The PA signal was recorded at multiple wavelengths and the maximum intensity was extracted, as illustrated in FIGS. 4A and 4B. In addition, center frequency and the full width at half maximum of each PA signal with the maximum intensity was calculated using its frequency spectrum, as illustrated in FIGS. 4C-4E, and the values were compared for the normal and osteoporotic cases. A decrease in the center frequency and bandwidth was observed for the osteoporotic case. Based on such analysis, Table 2 can be produced:

TABLE 3

| Femur neck | Bone density (g/cm$^2$) DEXA |
|---|---|
| C01: Normal | 1.057 |
| C02: Osteoporotic | 0.577 |

The PA signal of the biopsy bone samples was acquired using same experiment setup as described above. The specimens were extracted from the iliac crest. The femur bone mineral density (BMD) measured by DEXA for the corresponding patients is listed in Table 3 as follows.

TABLE 4

| Femur BDM (g/cm$^2$) measured by DEXA | | | | |
|---|---|---|---|---|
| C01 | C02 | C03 | C04 | C05 |
| 0.976 | 0.978 | 0.896 | 1.043 | 0.877 |

As illustrated in FIGS. 5A through 5C, the maximum intensity, center frequency, and the bandwidth of the detected PA signals at different wavelengths were extracted. The result showed that the sample with the highest bone mineral density (BMD) showed highest PA intensity, center frequency, and bandwidth in comparison to the other cases.

Therefore, the results of various experiments using the present approach for osteoporotic analysis in comparison to the normal cases showed a decrease of photoacoustic intensity spectrum, a shift of the frequency spectrum toward lower frequencies, and a decrease of the frequency spectrum bandwidth. This further shows that the present invention is advantageous over traditional analysis systems and methods, such as DEXA to measure BMD, for example, because DEXA uses ionizing radiation, is high cost, and is not sensitive to bone quality. On the other hand, the present invention provides systems and methods for utilizing the photoacoustic effects to perform non-destructive and radiation-free analysis that is closely linked to the target material and structural properties and is sensitive to architectural and mechanical features of the propagation medium.

Figure 19:
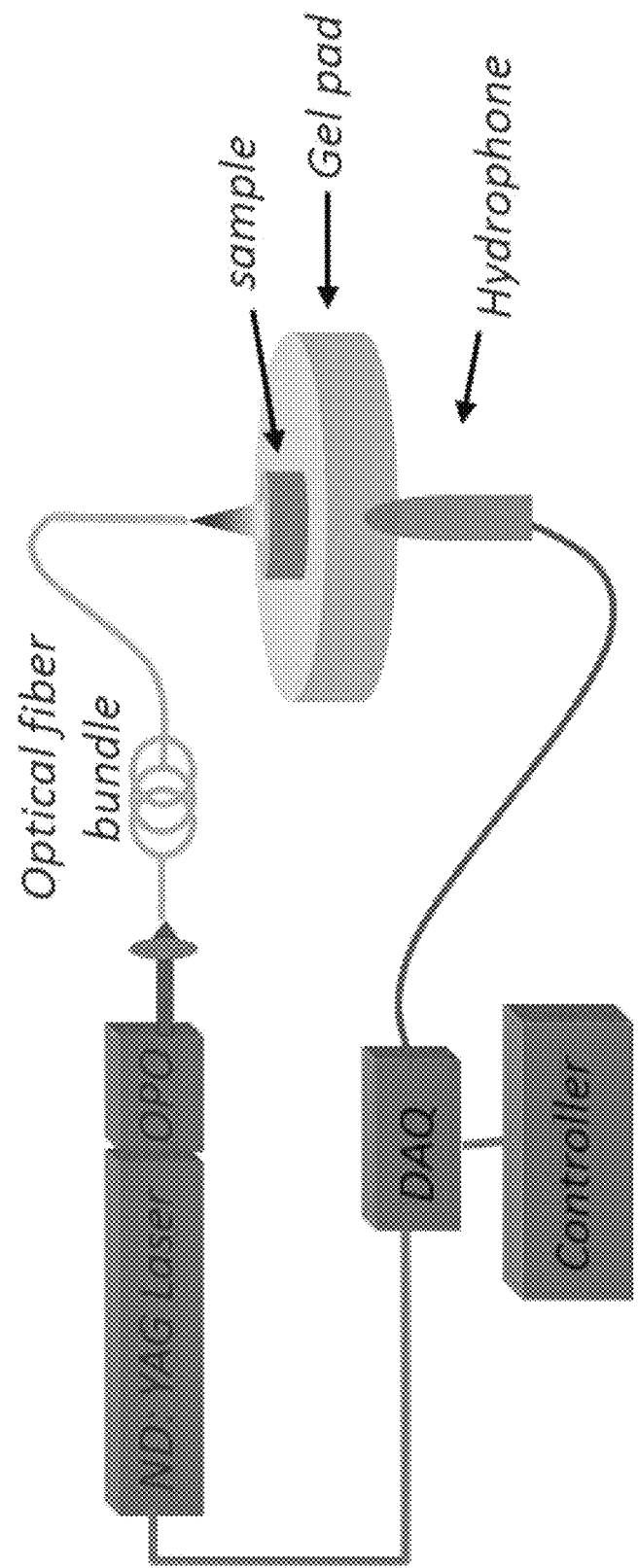
FIG. 19 is another example of an experimental setup for a phantom study, in accordance with aspects of the present disclosure.
Figure 20:
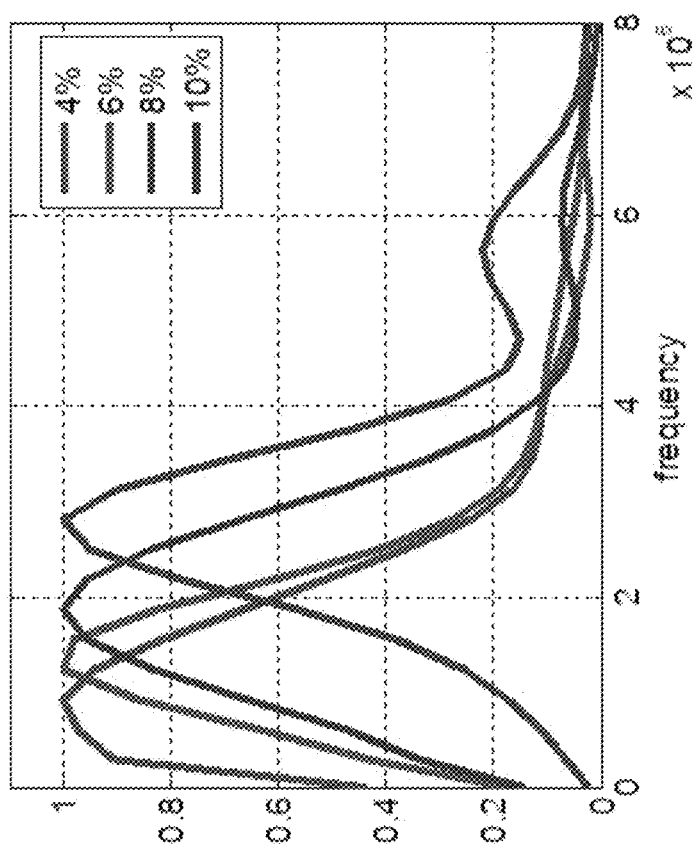
FIG. 20 is a graphical illustration depicting spectral differences between various gelatin sample types.
Figure 21:
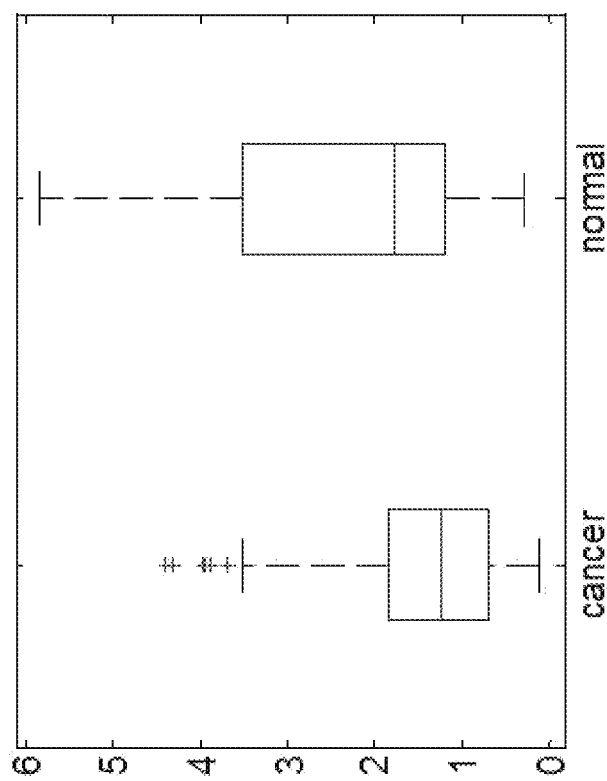
FIG. 21 is a graphical illustration depicting energy differences between normal and abnormal tissue.

In another application, systems and methods herein may be utilized to determine information related to normal as well as abnormal tissue. For instance, FIG. 19 shows an example experimental setup used characterizing tissue mechanical properties, in an approach that may help differentiate normal tissues from abnormal tissues. In the example of FIG. 19, tissue mimicking phantoms with different gelatin concentrations were imaged, and results are shown in FIG. 20. Specifically, PA frequency spectrums were shifted towards higher frequencies with increased gelatin concentrations. Additionally gelatin concentration was correlated with PA energy in the high frequency range, with $R^2=0.91$. In addition, as shown in FIG. 21, ex vivo thyroid tissues were evaluated. Malignant thyroid tissue was observed to contain approximated 1.5 times lower energy in the high frequency range in comparison to normal thyroid tissue (p.0.01).

In another application, systems and method of the present disclosure may be used for identifying and/or imaging a tissue or structure viscoelastistic properties and/or changes thereof. For instance, due to a logarithmic relationship between the PA signal phase delay and viscoelasticity, a PA signal phase delay can be measured to identify viscoelastic properties. Specifically, an intensity modulated continuous wave laser can be used to illuminate the subject. The recurring light absorption by target results in a periodic temperature variation that induces thermal stress. Due to this stress, strain is generated in the form of the PA waves. The strain also alternated periodically but because of the damping effect due to the viscoelasticity of biological tissues it would be out of phase with the stress. This means the generated PA signal is periodic and out of phase with the illumination. Hence, the phase lag between the dominant frequency of the generated PA wave and the reference signal that is used to modulate the excitation source can be measured, for example, using a lock-in amplifier.

As described, a PA signal may be induced by irradiating a region of interest using a short-pulsed, focused non-ionizing laser beam. Most of the delivered light energy will be absorbed, and converted into heat, leading to transient thermoelastic expansion and thus wideband ultrasonic emission. The generated and reflected ultrasonic waves are directly proportional to optical absorption in the region of interest and hence also dependent upon on medium temperature. Therefore, in some aspects, heat signatures and thermogenic volumes, and other thermal properties, can be measured directly using properly calibrated PA signals using systems and methods of the present disclosure. Such measured properties can be advantageous, for example, in accurately measuring temperatures of soft tissues deep inside a body, as well as determine the three-dimensional extend or volume of respective heat signature. Some thermal property measurement applications include determination of energy balance and metabolism conditions, for example, as related to brown adipose tissue (BAT).

Figure 13:
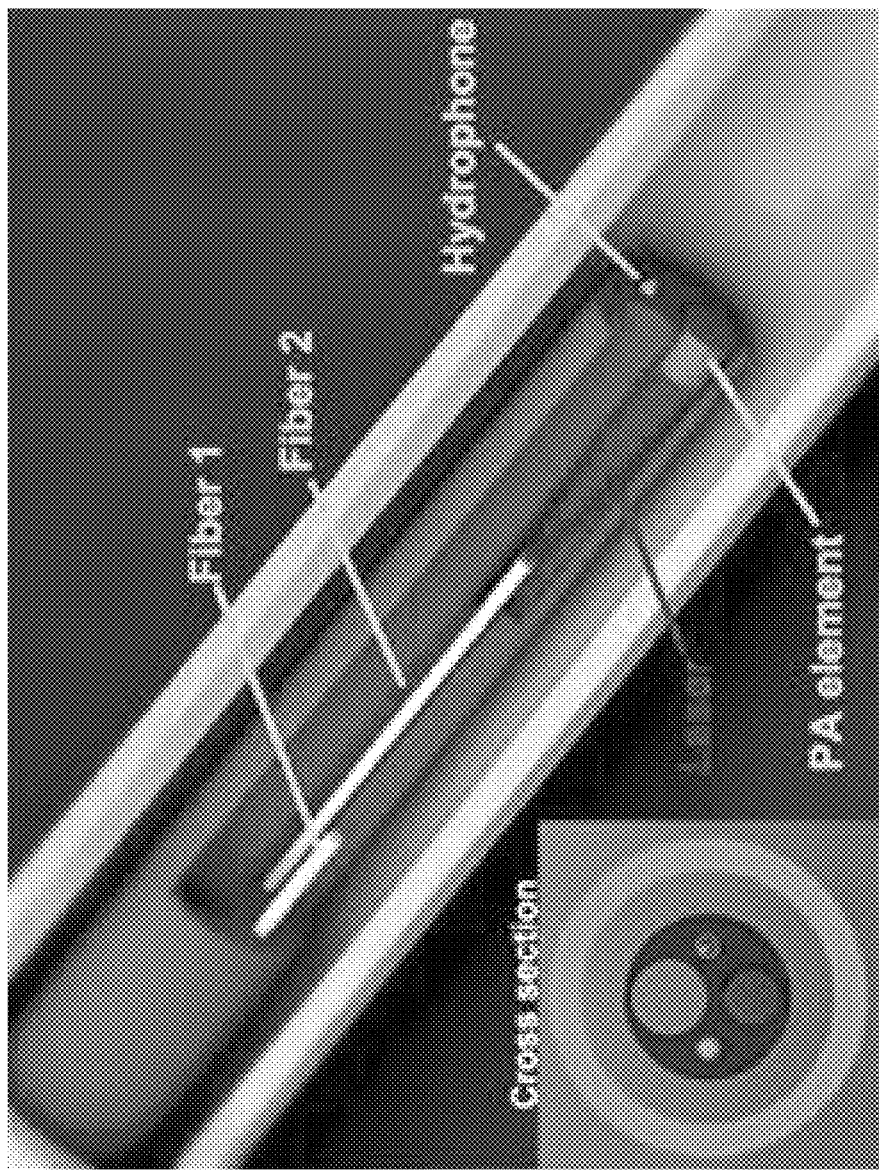
FIG. 13 is an example system for determining heat signature and/or thermogenic volumes, in accordance with aspects of the present disclosure.

By way of example, a system for determining heat signature and/or thermogenic volumes is shown in FIG. 13. The system includes a fiber-optic ultrasound sensing system integrated into a compact electromagnetic (EM) tracked tool. This system can exploit the photoacoustic effect to generate ultrasound signals, detectable by an optical fiber microphone. This configuration can produce A-mode ultrasound imaging showing tissue boundaries. In some designs, a channel to generate A-mode ultrasound based on PA effect may be used, while a second channel to emit pulsed laser energy to interact with tissues and BAT, and a third channel to host the fiber-optic hydrophone to receives ultrasound signals.

A photoacoustic sensitive material (i.e. membrane made of gold nanotubes or metal similar to brachytherapy seeds) may be placed at the end of the fiber. An ultrasound wave is generated perpendicular to this membrane as a result of PA effect. We rely on PA effect to produce ultrasound pulses, as described. In some aspects, the laser source may be a compact and low-cost pulsed laser diode (for example, with wavelengths 905 nm and 532 nm) and the driving circuit will provide pulses with duration 12 ns.

The optical-based hydrophone senses the acoustic signal (from either A-mode signal or the PA direct signal) by a micro Fabry Perot interferometer fabricated on the fiber tip. The fiber tip may include a reflector-polymer-reflector sandwich structure. Part of the laser beam may be reflected by the first reflective coating, and the rest reflected by the second one. This forms a Fabry-Perot interferometer. The interference between the two reflected beams is highly sensitive to the polymer layer thickness. When an ultrasound beam is applied, the mechanical vibration modulates the polymer layer thickness, as well as the optical signal intensity. Thus the ultrasound signal can be detected. A small aperture may also bring great omni-directionality, which is particularly suitable for this application. Most importantly, the hydrophone device also can measure temperature, which will be used as a ground-truth reading to facilitate calibration of PA imaging, as well as to provide true temperature measurements in the direction of the A-mode signal. The diameter of the hydrophone may be configured less than 100 micrometers, which can be introduced in the subject with minimal or no damage.

Figure 14A:
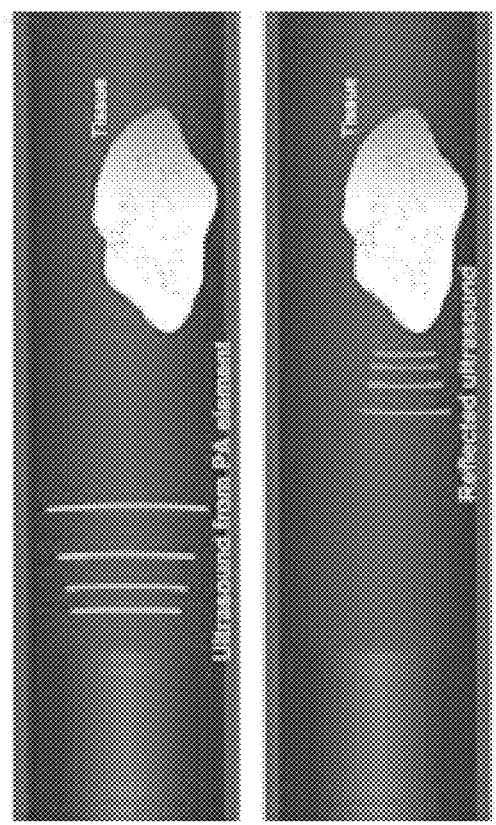
FIGS. 14A and 14B are a graphical illustrations of modes of image formation using backscattered ultrasound signals, in accordance with aspects of the present disclosure.
Figure 14B:
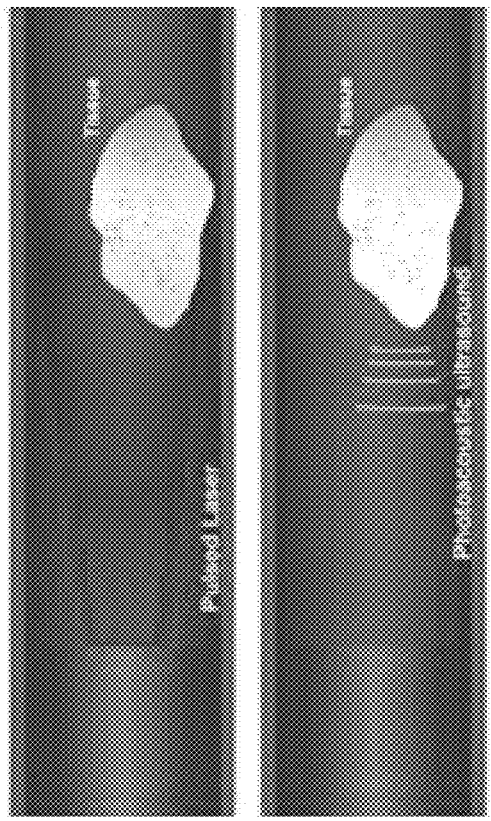

For A-mode ultrasound, an ultrasound pulse can be generated with the transmitter, as described above, and a signal can be acquired from the ultrasound receiver, as shown in FIG. 14A. For PA-mode imaging, an additional optical fiber embedded in the catheter can be used. As described, the fiber can be coupled to pulse laser sources with two different wavelengths (for example, 905 and 532 nm), which may be fired sequentially. Each pulse will produce PA signals from the tissue, corresponding to the optical absorption properties of the tissue (FIG. 14B). This configuration should increase temperature sensitivity. Additionally, a tracking system based on EM-technology may be incorporated to provide 6 degrees of freedom tracking information for all scanned A-lines and reconstructed 3D volumes.

Photoacoustic images may be susceptible to background noise artifacts which reduce Signal-To-Noise Ratio (SNR) and Contrast-to-Noise Ratio (CNR). Therefore, in accordance with aspects of the present disclosure, a spatial-angular compounding technique may also be implemented using systems and methods described herein. Such technique may be advantageous for use during free-hand photoacoustic imaging.

Figure 6:
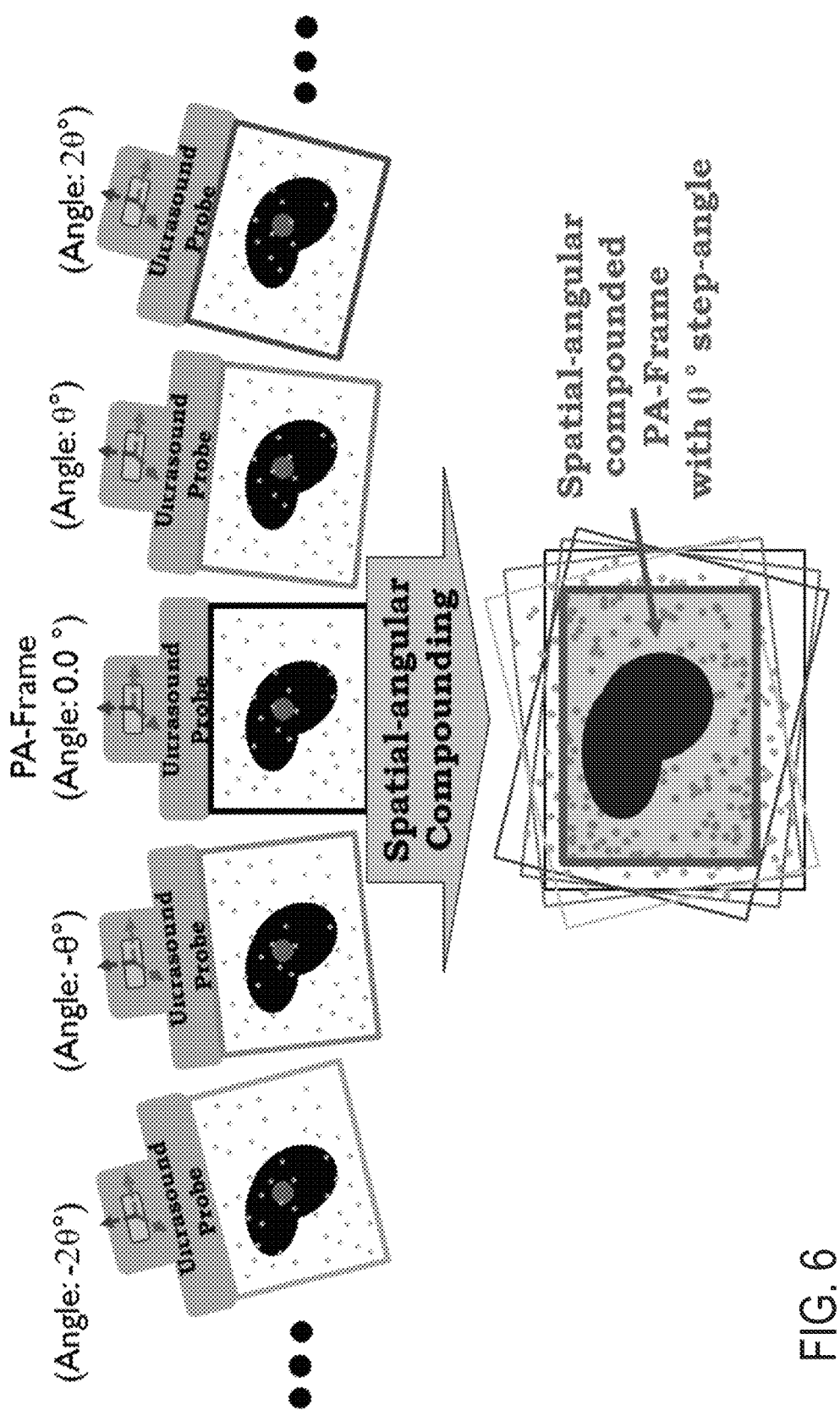
FIG. 6 is an illustration depicting a spatial-angular compounding technique, in accordance with aspects of the present disclosure.

A spatial-angular compounding technique utilizes multiple images obtained with similar elevational planes and varied elevational angles, as illustrated in the example of FIG. 6. An external tracker system, for example, as described with reference to FIG. 1B, may be used to provide pose information, including rotation and translation information, for each acquired photoacoustic image. Based upon provided pose information, frames in similar elevational planes may be filtered from the collected pre-beamformed RF data. These selected frames may be compounded, for example, using an averaging or selective averaging technique, applied to pre-beamformed RF data, beamformed RF data, and envelope-detected PA data, resulting in six different compounded image combinations.

Figure 7B:
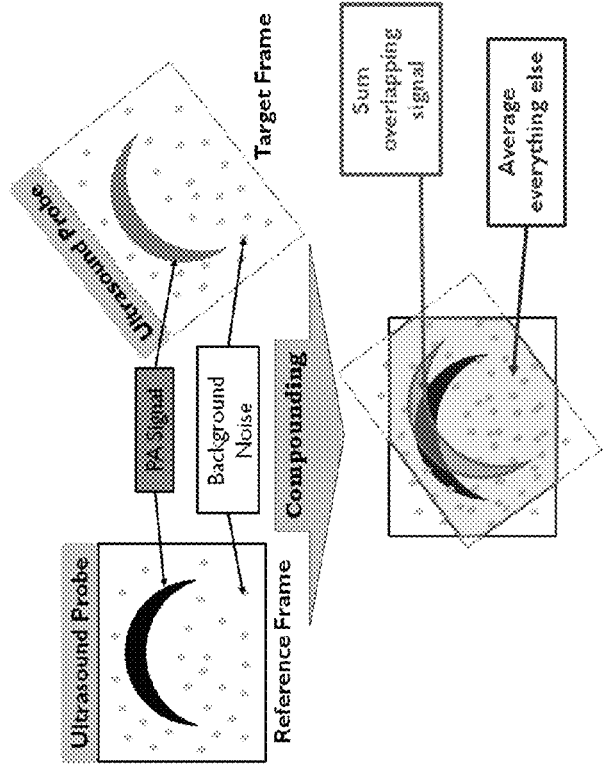
FIGS. 7A and 7B is an illustration depicting differences between frame averaging and selective frame averaging, respectively, in accordance with aspects of the present disclosure.
Figure 7A:
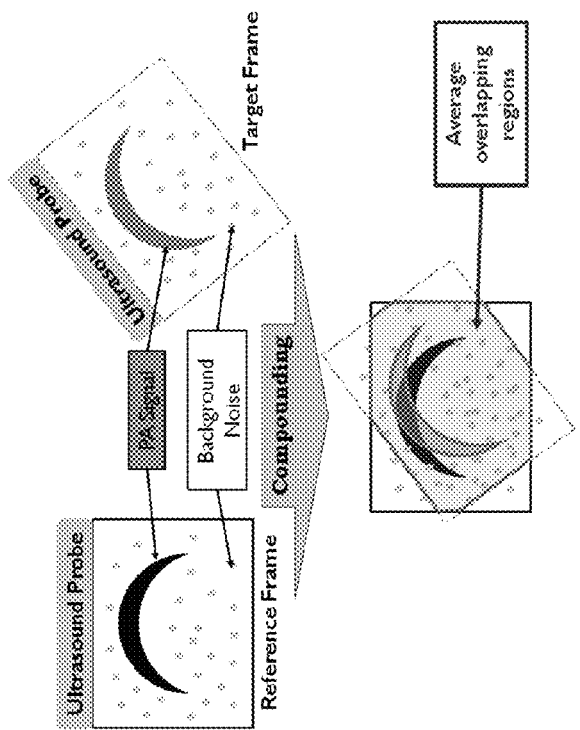
Figure 8:
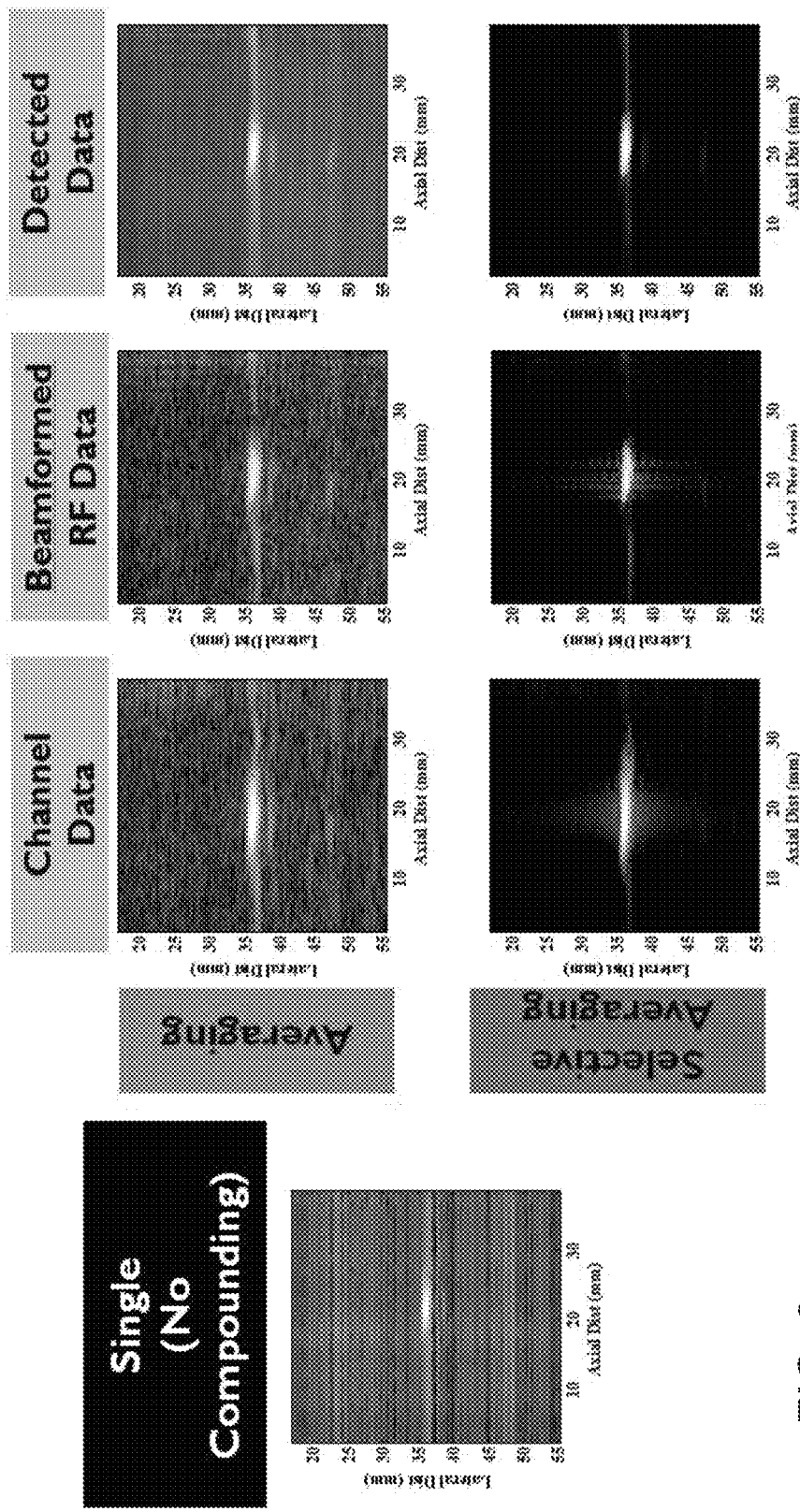
FIG. 8 is a graphical illustration showing example image data with and without compounding, in accordance with aspects of the present disclosure.
Figure 9:
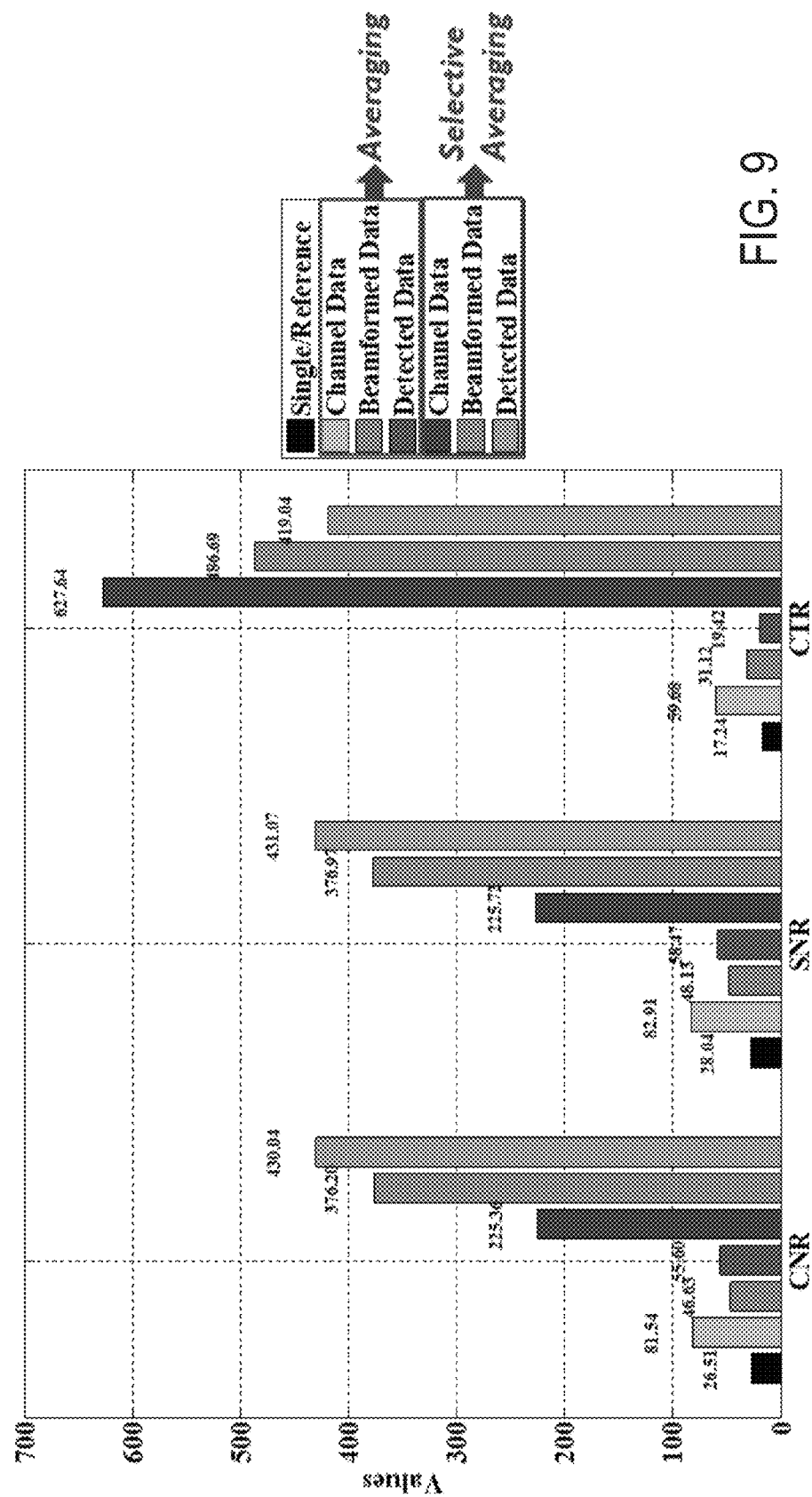
FIG. 9 is a graphical illustration comparing contrast-to-noise ratio (CNR), signal-to-noise-ratio (SNR), and contrast-to-tissue ratio (CTR) for images processed in accordance with aspects of the present disclosure.

As illustrated in FIG. 7A, averaging applies a mean operation to all filtered image frames. By contrast, as shown in FIG. 7B, selective-averaging is a dynamic compounding approach that uses image content information to sum overlapping regions of the photoacoustic signal, while applying conventional averaging to remaining regions. This approach may be applied once to each incoming frame and the dynamically updated compounded image. FIG. 8 is a graphical example comparing images generated either without compounding, or with average and selective averaging. As shown in FIG. 9 compounded PA images from each of the six compounding pipelines have higher CNR and SNR compared to a single PA image, while the selective-averaging method applied to envelope-detected data has the highest CNR and SNR.

Acquisition of ultrasound (US) pre-beamformed radio-frequency (RF) data is essential in advanced ultrasound imaging research such as adaptive beamforming, synthetic ultrasound imaging, and photoacoustic (PA) imaging. Specifically, PA imaging is an emerging medical imaging modality that relies on the absorption of optical energy and the subsequent emission of an acoustic wave. PA images include optical and acoustic information of the target material, and provide high contrast and high resolution medical images. Due to its merits, PA imaging is advantageous biomedical research for various structural and functional imaging applications.

Advanced 3D US image techniques such as 3D PA imaging can provide volumetric information for a target of interest. Therefore, a considerable number of studies have been conducted to generate 3D PA volumes. However, existing 3D PA systems require specifically designed motion stages, ultrasound scanner and data acquisition system to collect 3D pre-beamformed RF data. These systems are not compatible with clinical ultrasound systems and are difficult to reconfigure and generalize to other PA research.

In addition, 3D pre-beamformed RF data acquisition is more complicated than collecting 2D data, because reconstructing 3D volume data requires the spatial information of each 2D frame. Moreover, in the case of 3D PA volumes with a clinical 2D ultrasound scanner, we need to synchronize 2D PA frames and their corresponding spatial-tracking information. To overcome the limitation of existing 3D PA systems, a spatially-tracked pre-beamformed RF data acquisition technique with a freehand conventional 2D ultrasound transducer and an external tracking device may be used.

Figure 10:
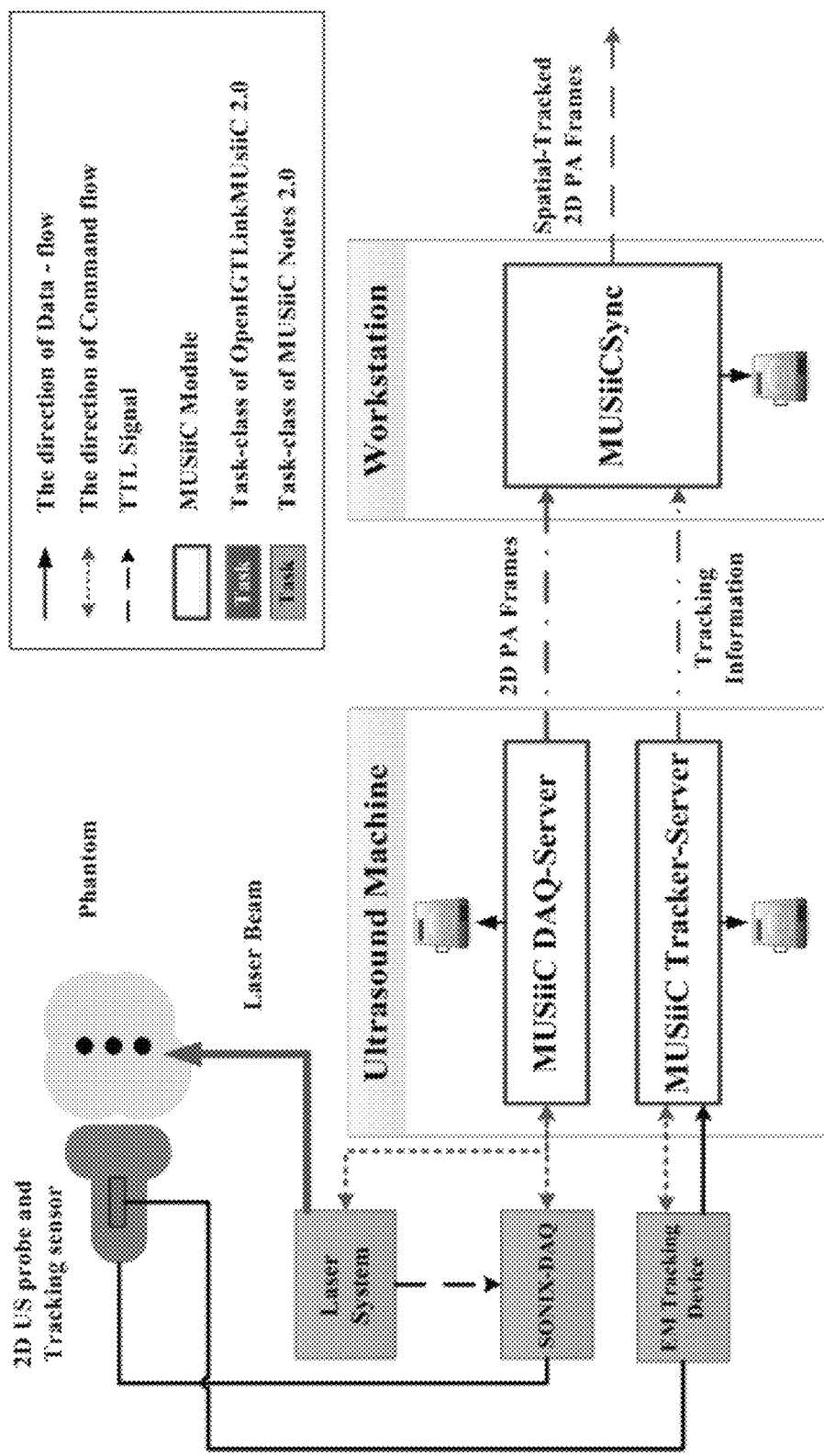
FIG. 10 is a system depicting a software framework for facilitating spatial-angular compounding, in accordance with aspects of the present disclosure.

A system for further facilitating spatial-angular compounding and use with systems and methods of the present disclosure is illustrated in FIG. 10. In particular, the system includes a software framework composed of several software modules and each software module connected by a TCP/IP connection.

As seen in the FIG. 10, the software framework is composed of three specialized executable modules: MUSiiC DAQ-Server 2.0, MUSiiC Tracker Server, and MUSiiCSync modules. MUSiiC DAQ-Server 2.0 collects 2D PA frames using SONIX-DAQ device (Ultrasonix Co.). MUSiiC Tracker Server acquires the spatial tracking information of an electromagnetic (EM) sensor attached to the 2D ultrasound transducer from the EM tracking device, 3D Guidance medSAFE (Ascension Technology Co.). The 2D PA frames and spatial tracking information, packed as USMessage of OpenIGTLinkMUSiiC and TrackingDataMessage of OpenIGTLink respectively, are transferred to the MUSiiCSync module. MUSiiCSync synchronizes these two data streams with their own timestamps and generates spatially-tracked PA frames.

To collect 2D PA frames from a conventional 2D ultrasound transducer, MUSiiC DAQ-Server 2.0 may be used with a SONIX-DAQ device and the provided Software Development Kit (SDK) from the manufacturer. FIG. 11 (a) represents a block diagram of this module. As seen in the figure, MUSiiC DAQ-Server may be composed of several sub task-classes from OpenIGTLinkMUSiiC 2.0 and MUSiiC Notes 2.0.

MUSiiC-DAQWrap class is a customized task-class of MUSiiC Notes2.0 for collecting pre-beamformed RF data efficiently. This task class controls the SONIX-DAQ device by using functions of the SDK and the laser-system with provided RS232C control protocols and the MUSiiC-RS232 task-class. The current DAQ device's SDK does not support a functionality for collecting pre-beamformed RF data in real-time. It only supports offline functionality, which requires data to be downloaded to a local hard disk. To address this limitation, MUSiiC-DAQWrap class has two task-threads to improve the performance of data acquisition: One task-thread controls SONIX-DAQ device and downloads data from the DAQ-device to local hard driver. Another task-thread loads the saved data and packs the data as USMessage of OpenIGTLinkMUSiiC 2.0.

To collect spatial-tracking information of the PA frames with an external EM tracking device, MUSiiC Tracker-Server was developed. MUSiiC-EMTrackerWrap class is also a customized task-class to collect tracking information from the device and generates TrackingDataMessage of OpenIGTLink. The collected USMessage and TrackingDataMessage can either be transferred to the MUSiiCSync module in real-time or saved to the local hard-disk by MUSiiC-TCPServer and MUSiiC-FileIO task-classes.

The main function of MUSiiCSync is to synchronize data from multiple data acquisition modules using the time-stamps associated to the data. This module also loads pre-computed US calibration information from the local hard disk, and applies this information to tracked 2D PA frames.

Figure 12:
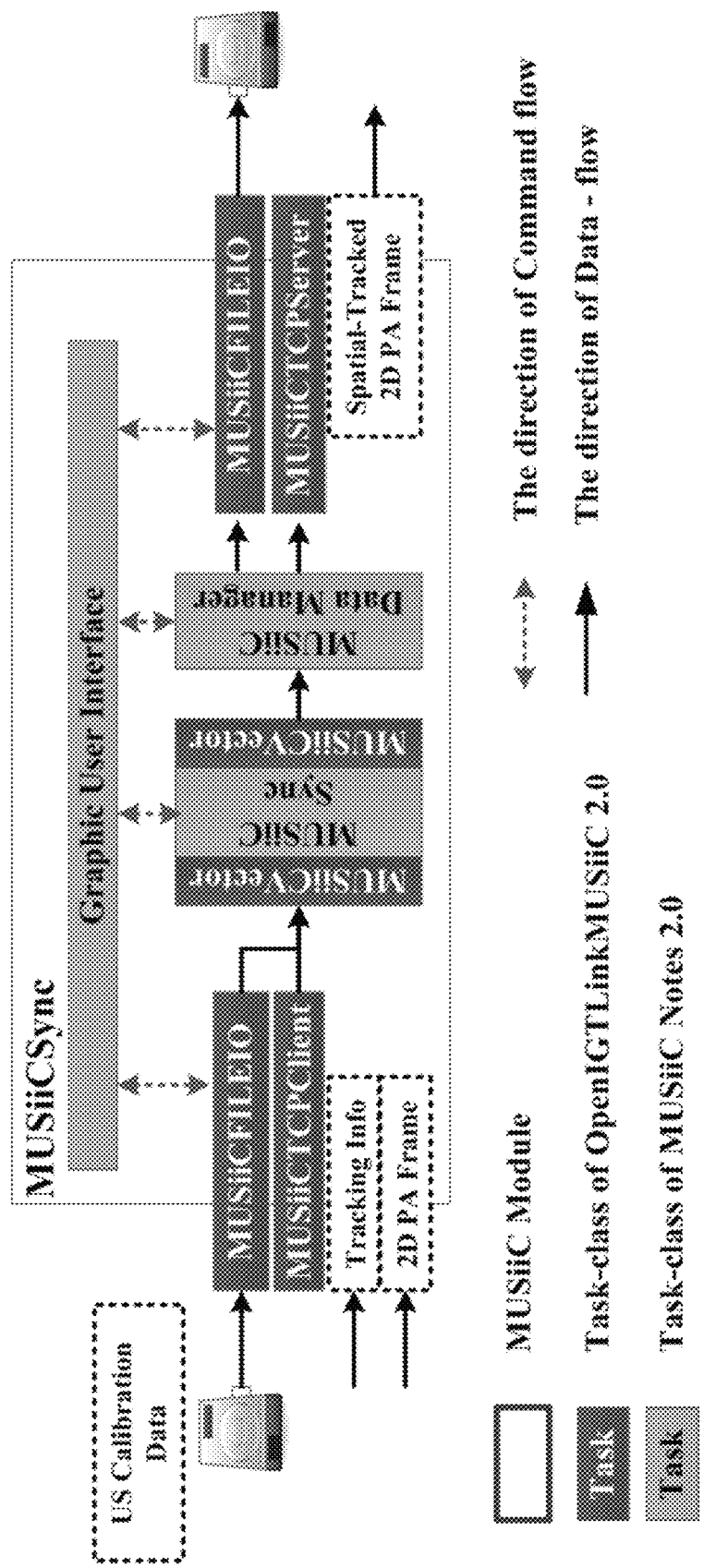
FIG. 12 is a block diagram depicting a module in the software framework of FIG. 10.

FIG. 12 represents the block diagram for MUSiiCSync. MUSiiCTCPClient class provides multiple TCP/IP connections to the TCP/IP server sockets of multiple data acquisition modules. Therefore, the MUSiiCSync module can receive data streams of USMessages and TrackingDataMessage from MUSiiC DAQ-Server and MUSiiC Tracker-Server simultaneously. The MUSiiCSync task-class of this module has two specific task-threads, Data-Collect and Data-Combine. The Data-Collect task-thread generates a MUSiiCSyncData instance with a frame of the incoming reference data and several frames of the additional data. The Data-Combine task-thread finds the frame of additional data with the closest timestamp to the timestamp of the reference data frame, and then combines them. In this step, this task-thread generates a spatially-tracked 2D PA frame by updating the tracking information of USMessage (2D PA frame) with the selected TrackingDataMessage (tracking information of US transducer) and pre-computed calibration data of the US transducer.

The above software framework can be used to collect spatially-tracked 2D PA frames with a freehand clinical 2D ultrasound transducer and an external tracking device. Our software framework is composed of specialized executable programs, MUSiiC DAQ-Server, MUSiiC Tracker Server and MUSiiCSync.

The acquisition speed of 2D PA frames on MUSiiC DAQ-Server may be limited by the repetition rate of the laser system, for example, at 10 Hz. On the other hand, MUSiiC Tracker-Server may collect spatial tracking information at approximately 110 Hz. Inside the MUSiiCSync module, 2D PA frames may be set as reference data and spatial tracking information may be set as additional data. In this case, the Data-Combine task-thread of MUSiiCSync class can find the tracking information that corresponds to a 2D PA frame and generate spatially-tracked 2D PA frames using pre-computed calibration information of the US transducer. It may be generally advantageous to set the data stream with the slower frame rate as the reference data, as it is more likely that a frame with a similar timestamp will be found from the data stream with a higher frame rate. The overall frame rate for generating spatially-tracked 2D PA frames on MUSiiCSync module is determined by the slowest frame rate of the incoming data streams.

The acquisition speed of 2D PA frames on MUSiiC DAQ-Server may be limited by the repetition rate of the laser system, for example, at 10 Hz. On the other hand, MUSiiC Tracker-Server collects spatial tracking information at approximately 110 Hz. Inside the MUSiiCSync module, 2D PA frames are set as reference data and spatial tracking information is set as additional data. In this case, the Data-Combine task-thread of MUSiiCSync class finds the tracking information that corresponds to a 2D PA frame and generates spatially-tracked 2D PA frames using pre-computed calibration information of the US transducer. It may be generally advantageous to set the data stream with the slower frame rate as the reference data, as it is more likely that a frame with a similar timestamp will be found from the data stream with a higher frame rate. The overall frame rate for generating spatially-tracked 2D PA frames on MUSiiCSync module is determined by the slowest frame rate of the incoming data streams.

The above software framework may be used for spatially-tracked pre-beamformed RF data acquisition with a freehand clinical 2D ultrasound scanner. MUSiiC DAQ-Server 2.0, MUSiiC Tracker Server and MUSiiCSync are the main modules of our software framework. Spatially-tracked 2D PA frames are collected efficiently using this software framework for 3D PA research and imaging. The software modules of the above software framework are based on the concept of network distributed modules and support multiple-client connections via TCP/IP network simultaneously. Moreover, the collected 2D PA frames are compatible with other modules of MUSiiC ToolKit 2.0 such as MUSiiC Beamform, B-Mode and MUSiiC Image-Viewer modules. These aspects easy reconfiguration and generalization to other PA or US systems.

As described, the present disclosure provides a variety of systems and methods that may be used alone or in combination to perform in vivo analysis of a subject. Specifically, systems and methods described herein utilize the photoacoustic effect to investigate properties or features of targeted tissues structures, including mechanical properties, optical properties, thermal properties, and so forth. That is, optical energy generated using systems described herein, is absorbed by a targeted tissues or structures and subsequently produces thermal expansions in the targeted tissues or structures. The excitations result in propagating acoustic and/or elastic waves, which may be captured using ultrasound probes, and other acoustic devices. The waves contain information related to the provided excitation, as well as the properties of tissues and structures, which when properly acquired and analyzed, as described in various embodiments of the present disclosure, can be utilized to identify a condition of the subject, such as the presence of osteoporosis.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for performing in vivo analysis of a subject, the system comprising:

an excitation source configured to direct an electromagnetic excitation toward the subject;

an ultrasound probe configured to acquire data about resultant waves caused by the electromagnetic excitation;

a tracking system configured to track a position of at least one of the excitation source, a position of the electromagnetic excitation, and a position of the ultrasound probe;

a processor configured to:
receive the data from the ultrasound probe;
process the received data to extract information related to properties of tissues in the subject;
compare the information related to the properties of tissues in the subject using a set of criteria; and
generate a report about a condition of the subject based on the comparison of the information related to properties of the tissues in the subject.

2. The system of claim 1, wherein the processor is further configured to process the data to generate at least one of images of the subject and spectroscopy information about the subject.

3. The system of claim 1, wherein the excitation source is further configured to modulate a wavelength of the electromagnetic excitation.

4. The system of claim 1, wherein the properties of tissues in the subject include mechanical properties, or optical properties, or thermal properties, or combinations thereof.

5. The system of claim 1, wherein the processor is further configured to determine changes in the properties of tissues in the subject by comparing the data to at least one of a baseline dataset and a prior dataset acquired from the subject.

6. The system of claim 1, wherein the processor is to determine at least one of broadband ultrasound attenuation (BUA) and a speed of sound (SOS) from the data.

7. The system of claim 1, wherein the condition of the subject includes at least an indication of a presence of an osteoporotic bone.

8. The system of claim 1, wherein the condition of the subject includes an indication of at least one of a low and a high bone density.

9. A system for performing in vivo analysis of a subject, the system comprising:

an excitation source configured to generate an electromagnetic excitation;

a delivery system configured to receive the electromagnetic excitation from the excitation source and direct the electromagnetic excitation toward the subject;

an ultrasound probe configured to acquire data from the subject about resultant waves caused by the electromagnetic excitation; and a holder configured to engage the ultrasound probe and at least a portion of the delivery system to provide an adjustable relative coupling between the ultrasound probe and the portion of the delivery system.

10. The system of claim 9, wherein the adjustable relative coupling is configured to adjust at least one of an angle and a depth of delivery of the electromagnetic excitation to the subject.

11. A system for performing in vivo analysis of a subject, the system comprising:

an excitation source configured to generate an electromagnetic excitation;

a delivery system configured to receive the electromagnetic excitation from the excitation source and direct the electromagnetic excitation toward the subject;

an ultrasound probe configured to acquire data from the subject about resultant waves caused by the electromagnetic excitation; and a tracking system configured to track a position of at least one of the delivery system and the ultrasound probe.

12. The system of claim 11, wherein the tracking system includes at least one of an electromagnetic and an optical tracker configured to track a location of the at least one of the delivery system and the ultrasound probe.

13. The system of claim 11, further comprising a user feedback system configured to provide feedback to a user to select a desired relative position of the delivery system relative to the ultrasound probe.

14. The system of claim 11, wherein the tracking system includes a delivery system tracking subsystem and an ultrasound probe tracking subsystem.

15. The system of claim 14, wherein the delivery system tracking subsystem and the ultrasound probe tracking subsystem operate independently.

* * * * *